US012644082B2

(12) United States Patent
Nefigmann

(10) Patent No.: US 12,644,082 B2
(45) Date of Patent: Jun. 2, 2026

(54) CARBON DIOXIDE-NEUTRAL BIO CONVERTER FACILITIES FOR PRODUCING BIOGAS USING HYDROGEN AND ACTIVATED CARBON COMPOSITIONS IN THE FERMENTATION LIQUID OF THE BIO CONVERTER

(71) Applicant: NEFIGMANN GMBH, Steinfurt (DE)

(72) Inventor: Sven Nefigmann, Steinfurt (DE)

(73) Assignee: NEFIGMANN GMBH, Steinfurt (DE)

( * ) Notice: Subject to any disclaimer, the term of this patent is extended or adjusted under 35 U.S.C. 154(b) by 759 days.

(21) Appl. No.: 18/000,079

(22) PCT Filed: May 5, 2021

(86) PCT No.: PCT/EP2021/000058
§ 371 (c)(1),
(2) Date: Nov. 28, 2022

(87) PCT Pub. No.: WO2021/228428
PCT Pub. Date: Nov. 18, 2021

(65) Prior Publication Data
US 2023/0279321 A1 Sep. 7, 2023

(30) Foreign Application Priority Data
May 9, 2020 (DE) ..................... 10 2020 002 755.5

(51) Int. Cl.
*C12M 1/107* (2006.01)
*C01B 3/047* (2026.01)
*C12P 5/02* (2006.01)

(52) U.S. Cl.
CPC ............. *C12M 21/04* (2013.01); *C01B 3/047* (2013.01); *C12P 5/023* (2013.01)

(58) Field of Classification Search
CPC .......... C12M 21/04; C01B 3/047; C12P 5/023
(Continued)

(56) References Cited

U.S. PATENT DOCUMENTS 3,198,604 A 8/1965 Pfefferle
3,957,534 A 5/1976 Linkohr et al.
(Continued)

FOREIGN PATENT DOCUMENTS

DE 2307853 A1 9/1974
DE 60221141 T2 10/2007
(Continued)

OTHER PUBLICATIONS

DE-102014111287-A1 Machine English Translation (Year: 2016).*
(Continued)

*Primary Examiner* — Michael L Hobbs
*Assistant Examiner* — Lenora A Abel
(74) *Attorney, Agent, or Firm* — Steinfl + Bruno LLP

(57) ABSTRACT
A carbon dioxide-neutral biodigester plant includes a biodigester for carbon dioxide-neutral, single-stage or multi-stage production of biogas by fermentation of biomass in a fermentation liquid agitated in presence of elemental hydrogen, hydrogenotrophic and methanogenic archaea, and activated carbon masses, a source of ammonia connected to a first ammonia line, an ammonia cracker to produce hydrogen or a hydrogen-nitrogen mixture by catalytic cracking of ammonia, a first hydrogen line for feeding the produced hydrogen or the hydrogen-nitrogen mixture directly into the biodigester, and a treating device for treating activated coal masses with hydrogen at higher pressure. The treating device includes a pressure line and a treating spray lance. Hydrogen-containing activated coal masses configured as spray cones are injected into the fermentation liquid of the biodigester.

12 Claims, 4 Drawing Sheets

(58) Field of Classification Search

USPC .................................................. 435/300.1

See application file for complete search history.

(56) References Cited

U.S. PATENT DOCUMENTS

| | | | |
|---|---|---|---|
| 7,285,153 B2 | 10/2007 | Bruun et al. | |
| 8,288,600 B2 * | 10/2012 | Bartek .................. | C10G 11/18 |
| | | | 208/143 |
| 8,691,182 B2 * | 4/2014 | Grannell ................ | F23D 14/62 |
| | | | 423/658.2 |
| 10,005,994 B2 * | 6/2018 | Stephens .................. | C12P 7/40 |
| 2009/0277331 A1 | 11/2009 | Li et al. | |
| 2012/0088266 A1 | 4/2012 | Gray | |
| 2012/0100590 A1 | 4/2012 | Tartakovsky et al. | |
| 2017/0184015 A1 * | 6/2017 | Andren .................. | C12M 23/44 |
| 2019/0084831 A1 | 3/2019 | Andersen et al. | |

FOREIGN PATENT DOCUMENTS

| | | | | |
|---|---|---|---|---|
| DE | 102008048062 B3 | 4/2010 | | |
| DE | 102014100849 A1 | 7/2015 | | |
| DE | 102014100850 B4 | 9/2015 | | |
| DE | 102014111287 A1 * | 2/2016 | ............. | C12P 5/023 |
| DE | 102015012436 A1 | 3/2017 | | |
| DE | 102016004026 A1 | 10/2017 | | |
| DE | 102018117281 A1 | 1/2020 | | |
| DE | 102019006623 A1 | 3/2021 | | |
| EP | 1444475 B1 | 7/2007 | | |
| EP | 2007680 B1 | 8/2012 | | |
| EP | 2661511 B1 | 4/2016 | | |
| EP | 3028990 B1 | 8/2017 | | |
| EP | 3028909 B1 | 10/2019 | | |
| EP | 3613708 A1 | 2/2020 | | |
| EP | 3632543 A1 | 4/2020 | | |
| JP | 2009059933 A | 3/2009 | | |
| JP | 2018021089 A | 2/2018 | | |
| WO | 2006/017022 A3 | 3/2006 | | |
| WO | 2011/003081 A1 | 1/2011 | | |

OTHER PUBLICATIONS

International Search Report and Written Opinion for International PCT Application No. PCT/EP2021/000058 filed on May 5, 2021, on behalf of Nefigmann GMBH, Mail Date: Sep. 8, 2021, 36 Pages, with English Translation.

Jade Boyd, "Light makes Rice U. catalyst more effective," Oct. 4, 2018, Retrieved from http://news.rice.edu/2018/ 1 0/04/light-makes-rice-u-catalyst-more-effective-2/, 5 pages.

Rödger et al., "Stimulation of Biogas production by adding Biochar" in Müll und Abfall, 2014, 9:13, 476-480, 7 pages.

Zhu et al., "Facile hydrogen/nitrogen separation through graphene oxide membranes supported on YSZ ceramic hollow fibers," Journal of Membrane Science, vol. 535, Aug. 1, 2017, pp. 143-150.

* cited by examiner

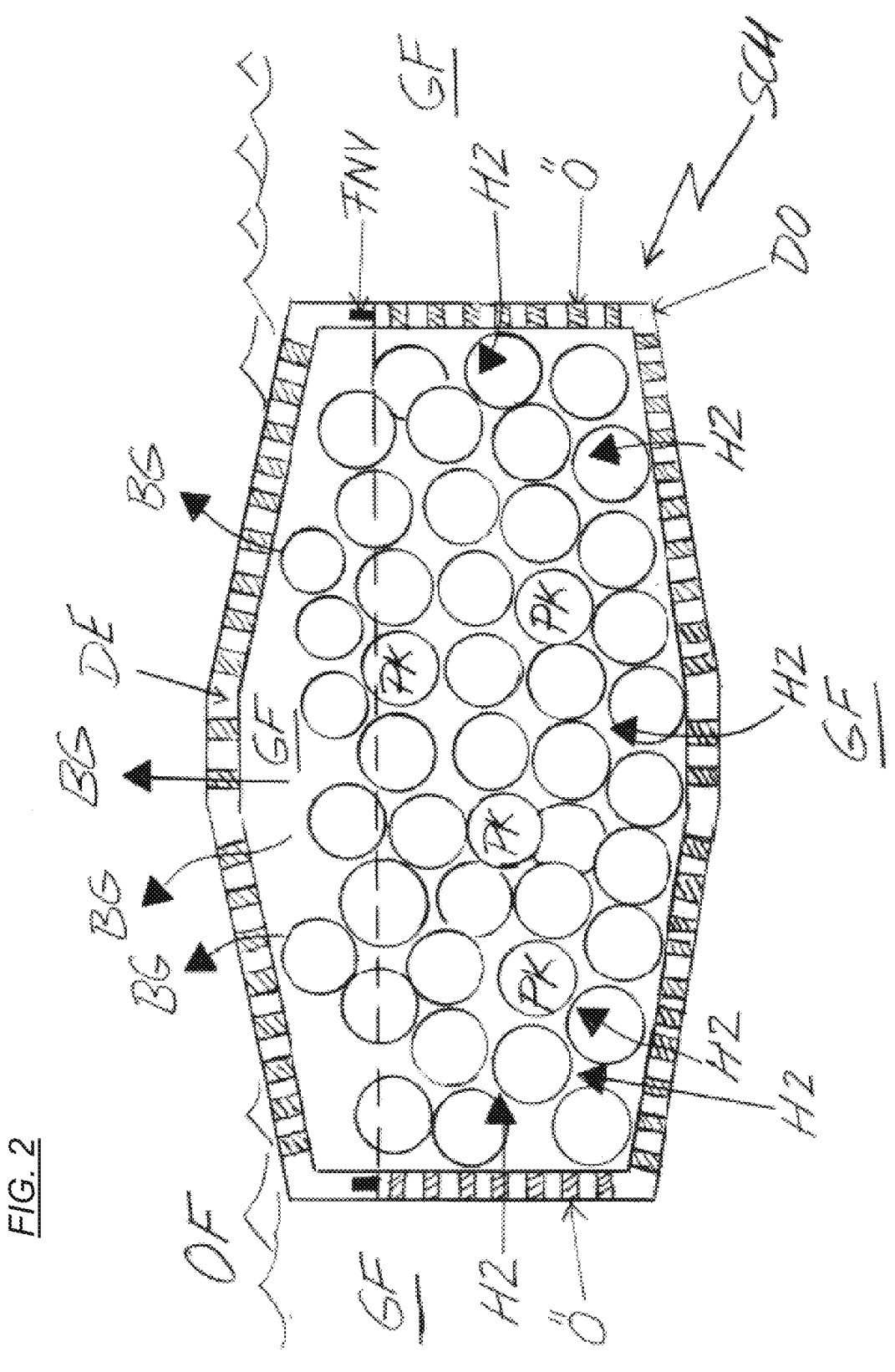
_FIG. 2_

CARBON DIOXIDE-NEUTRAL BIO CONVERTER FACILITIES FOR PRODUCING BIOGAS USING HYDROGEN AND ACTIVATED CARBON COMPOSITIONS IN THE FERMENTATION LIQUID OF THE BIO CONVERTER

FIELD OF INVENTION

The present invention relates to carbon dioxide-neutral biodigester plants for the production of biogas with elemental hydrogen and activated carbon masses in the fermentation liquid of the biodigesters.

In addition, the present invention relates to carbon dioxide-neutral digestion processes for the production of biogas in biodigesters by fermentation of biomass in a fermentation liquid agitated with agitation means in the presence of elemental hydrogen, hydrogenotrophic and methanogenic archaea and activated carbon masses.

Last but not least, the present invention relates to the use of the digested biomasses and fermentation products produced by the carbon dioxide-neutral digestion processes and/or the activated carbon masses used in the process as fertilizer or for the production of terra preta.

STATE OF THE ART

In order to obtain methane gas, biomass is anaerobically fermented in biodigesters. In the context of the present invention, the term "fermentation" is understood to mean the digestion of biological, in particular organic, materials with the aid of microorganisms (bacteria, fungi and/or other cell cultures). However, fermentation can also be accomplished by the addition of metabolically activated enzymes or other biologically activated molecules, such as nutrient substrates of the microorganisms. Fermentation may include aerobic processes, e.g., acetic acid fermentation, as well as anaerobic processes, e.g., lactic acid fermentation.

In their article "Increasing Biogas Yield by Adding Plant Charcoal" in Müll und Abfall, 2014, pages 476 to 480. Dipl. Wi.-Ing. Jan-Markus Rödger, M. Eng.-M. Sc. Waldemar Ganagin, Dipl.-Ing.agr. Andreas Krieg, B. SC. Christian Roth, and Prof. Dr.-Ing. Achim Loewen discuss the increase of biogas yield by the addition of plant carbon. In this article it is shown that by adding large charcoal particles to the secondary digester, the additional yield of methane gases is increased by 24% within 91 days.

The German patent application DE 10 2014 111 287 A1 discloses a process for producing methane in biodigesters from biomass, in which hydrogen is fed to the biodigesters. The hydrogen is preferably obtained by the electrolysis of water. The co-use of activated carbon masses is not described.

German patent application DE 10 2015 012 436 A1 discloses the use of carbon nanoparticles, carbon microparticles and/or carbon macroparticles to promote the growth of microorganisms and/or to increase the metabolism and/or catabolism and/or anabolism and/or to increase the yield of various products and/or to protect the concrete walls in digesters.

German patent DE 10 2016 004 026 B4 discloses the use of floats with activated carbon mass to increase the methane yield during digestion of the fermentation liquid.

U.S. patent application US 2012/0100590 A1 discloses a biodigester for the production of methane with electrolysis cells for the electrolysis of water. The fermentation liquid contains hydrogenotrophic and methanogenic archaea. The co-use of activated carbon masses in the fermentation or digestion of the fermentation liquid is not described.

U.S. patent application 2012/0088266A1 describes a biodigester for the production of hydrogen by a hydrogen-producing bacterial mixture in a fluidized bed. The fluidized bed contains activated coal particles and particles of steel, gravel, glass and coal ash coated therewith. The known biodigester is not suitable for the production of methane.

The unpublished German patent application dated Sep. 22, 2019, with the file number 10 2019 006 623.5, describes a biodigester for the single-stage or multi-stage production of biogas by fermentation of biomass in a fermentation liquid agitated with agitation means in the presence of elemental hydrogen, hydrogenotrophic and methanogenic archaea and activated carbon masses. The elemental hydrogen is produced in situ and/or outside the fermentation liquid by electrolysis of water in at least one internal and/or external electrolysis cell. In this process, the electrolysis cells are protected from direct contact with the activated carbon masses. The hydrogen can also be introduced into the fermentation liquid from an external hydrogen supply. Examples of suitable external hydrogen supplies are compressed gas cylinders and pressure vessels filled with metal hydrides such as aluminum hydride or lithium aluminum hydride, which release the elemental hydrogen again at higher temperatures. However, the hydrogen can also be introduced into the fermentation liquid from a hydrogen-producing biodigester together with carbon dioxide.

From the American patent application US 2019/0084831 A1 a process for cracking preheated ammonia at a temperature of 500° C. to 1100° C. is known. Nickel oxides, iron oxides, manganese, platinum, palladium, lanthanum oxides, molybdenum and/or zirconium are used as cracking catalysts. A nickel catalyst supported on magnesium-aluminum spinel is particularly preferred. The resulting hydrogen-nitrogen mixture is cooled to 40° C. to 300° C., freed from residual ammonia and used as fuel for turbines.

European patent EP 2 007 680 B1 discloses the use of zirconium oxide nitride catalysts for the decomposition of ammonia into hydrogen and nitrogen. The catalysts are said to be particularly suitable for fuel cells.

Japanese patent application JP 2018021089 W discloses a zeolite-based cracking catalyst for ammonia in a fuel cell that is designed not to aggregate. The actual catalysts are metal microparticles.

From the Japanese patent application JP 2009059933 A a cracking catalyst for ammonia is known which is composed of a carrier of cerium oxide, aluminum oxide and zirconium oxide and contains at least one transition metal.

Furthermore, a process for cracking ammonia into a gas mixture of 75% hydrogen and 25% nitrogen is known from European patent 3 028 909 B1. The gas mixture is burned for heating purposes with air as the oxidant or used as fuel in a heat/power engine. Before use in a boiler or heat/power engine, further ammonia can be added to increase the energy content.

The use of hydrogen-nitrogen mixtures produced by the catalytic cracking or cracking of ammonia in biodigesters containing activated coal masses is not described.

It would be desirable to use activated carbon masses containing absorbed or adsorbed hydrogen as a process material. Unfortunately, however, the absorption capacity of activated carbon for hydrogen is very low at the process temperatures.

Recently, attempts have been made to achieve a fuel cell revolution by using activated carbon storage made of bamboo. With the activated carbon storage system, 60 g of hydrogen can be stored in 20 g of bamboo activated carbon at 1 bar—but only at −196° C. (INGENIEUR.de Technik-Karriere—News, 30 Oct. 2018).

Binary tetrahydrofuran-hydrogen-chlathrate hydrates have already been investigated for their hydrogen storage capacity for a long time. It is not known whether they can be used as process materials, possibly together with activated carbon, in biodigesters.

OBJECT OF THE INVENTION

The present invention was based on the task of providing carbon dioxide-neutral biodigester plants in which the methane yield is even higher than in known biodigesters. In addition, the methane obtained should have a high degree of purity. At the same time, the carbon dioxide-neutral digestion process in question should be carried out easily and safely, and the activated coal masses used should be separable in a simple manner. Last but not least, hydrogen sources for the carbon dioxide-neutral biodigester plants are to be provided which no longer present the problems of storing hydrogen as a gas or as a metal hydride, but by means of which hydrogen can be produced safely as required.

Solution According to the Invention

Accordingly, the carbon dioxide-neutral biodigester plants for single-stage or multi-stage carbon dioxide-neutral production of biogas by fermentation of biomass in a fermentation liquid agitated with agitation means in the presence of elemental hydrogen and hydrogenotrophic and methanogenic archaea and activated carbon mass according to the independent patent claim 1 was found.

In the following, this carbon dioxide-neutral biodigester plant will be referred to as the "biodigester plant according to the invention".

Moreover, the carbon dioxide-neutral, single-stage or multi-stage process for producing biogas with the aid of the biodigester plant according to the invention, is hereinafter referred to as the "digestion process according to the invention".

Furthermore, the process for injecting hydrogen-containing powdered activated carbon masses into the fermentation liquid of a biodigester is hereinafter referred to as the "injection process according to the invention".

Last but not least, the use of the digested biomasses or fermentation products produced by the digestion process according to the invention as well as of the activated coal masses used in the digestion process according to the invention as fertilizer and for the production of terra preta, is hereinafter referred to as the "use according to the invention".

Advantages of the Invention

With regard to the prior art, it was surprising and not foreseeable for the person skilled in the art that the task underlying the present invention could be solved with the aid of the biodigester plant according to the invention, the digestion process according to the invention, the injection process according to the invention and the use according to the invention.

Surprisingly, a significant increase in methane yield was achieved by the biodigester plant and digestion process according to the invention.

By placing the activated coal masses in the biodigester plants according to the invention in floats, floating bodies, solid layers, immobile fluid-permeable vessels, fluidized bodies of a fluidized bed, magnetizable particles and/or a fixed bed, the activated and/or passive abrasion and removal and/or erosion could be suppressed. This had the advantage that the activated carbon masses decomposed more slowly than the biomass.

The recovery of the activated coal masses no longer occurred by the participation in the stock stream. This resulted in a longer residence time of the activated coal masses in the digestion process according to the invention, whereby also the microorganisms introduced by inoculation had a longer residence time.

Before and/or during the digestion process according to the invention, the activated carbon masses could be loaded with trace elements, microelements, ultra-trace elements, ultra-microelements, bulk elements, nutrients, essential nutrients, carbohydrates, fats, proteins, minerals and/or vitamins.

In particular, it was surprising that heavy metals could be bound by the activated carbon masses, which meant that the digested biomasses or fermentation products had particularly low heavy metal values. This meant that they could be excellently used as fertilizers or for the production of Terra Preta.

Because the activated coal masses used in the digestion process according to the invention bound these heavy metals particularly tightly by adsorption and chemisorption and no longer released them into the environment, they could also be used excellently for the production of terra preta and as fertilizer.

Other valuable fertilizers and starting products for terra preta could be obtained by combining the digestion products and related activated charcoal masses.

The main advantage, however, was that the hydrogen in the biodigester plants according to the invention could be made available as needed in catalytic ammonia crackers, so that it was not necessary to stockpile hydrogen, but only ammonia.

The other major advantage was the particularly high yield of methane of a purity >90 vol. %, preferably >95 vol. %. In addition, the almost complete or total digestion of carbon dioxide into methane meant that a complex and expensive gas scrubber with NaOH could be dispensed with.

The essential advantage of the biodigester plant according to the invention, however, was its carbon dioxide-neutrality. It could also be designed in such a way that it even served as a carbon dioxide sink.

DETAILED DESCRIPTION OF THE INVENTION

The biodigester plant according to the invention and its peripherals, which include a central electronic control unit or data processing system, electronic, mechanical, hydraulic control circuits, measuring instruments, flow meters, gas meters, pressure gauges, pressure relief valves, throttle valves, pressure maintaining valves, flow valves, actuators, transport lines for liquids, gases, slurries and solids, energy sources, power sources, pumps and viewing windows are constructed of mechanically stable, acid and base stable, corrosion stable, temperature stable, pressure stable and dimensionally stable materials. Examples of suitable materials include steel, stainless steel, chrome steel, anodized aluminum, metal alloys, thermoplastic and thermoset plastics, concrete, ceramics, glass ceramics, and glasses.

All commonly used biomasses containing carbon-carbon bonds can be considered for the biodigester plant and the preservation process according to the invention.

Examples of suitable biomasses are manure, slurry, fecal matter, digestate, dry ferments, sewage sludges, ferments, composts, biowastes, vegetable wastes, leaves, lumber, mashes, pomace, food industry wastes, biotechnological wastes, genetically engineered wastes, animal wastes, celluloses, hemicelluloses, lignocelluloses, biomasses and wastes containing celluloses, hemicelluloses and/or lignocelluloses, high molecular weight proteins and structural proteins, concentrates from the biological treatment stages of wastewater treatment plants, chemical scrubbers and filters, wastewater, solid deposits from exhaust air treatment, foodstuffs, feedstuffs, seaweed, aquatic plants, algae and organic compounds produced by hydrolysis, acidogenesis and acetogenesis, such as carboxylic acids and their esters.

Other examples of suitable biomasses include, in particular, farm manure such as cattle slurry, pig slurry, cattle manure, poultry manure and horse manure without straw, renewable raw materials such as corn silage, whole-plant cereal silage (GPS), green rye silage, cereal grains, grass silage, sugar beets, fodder beets, sunflower silage, Sudan grass, sugar millet and green rye, substrates from the processing industry such as brewer's grains, grain stillage, potato stillage, fruit stillage, crude glycerol, rapeseed press cake, potato pulp, Z-pressed pulp, molasses, apple pomace, grape pomace and green and lawn cuttings such as green cuttings.

Furthermore, reference is made to >List "Biogenic waste and waste with relevant biogenic fractions" in accordance with § 3 para. 6 of the 2009 funding guidelines for environmental funding in Austria, Kommunal Kredit Public Consulting, Version August 2018, Kommunalkredit Public Consulting GmbH, Vienna< and to >"Was ist bei der landwirtschaftlichen Verwertung von Bioabfällen zu beachten?", LfL, Bayerische Landesanstalt für Landwirtschaft, 3rd edition, May 2013 (Internet only)<.

By using the biomasses listed above, by-products from agriculture can be particularly utilized for the methane production and thus can be significantly reduced.

The biomasses are typically fed into the fermentation liquid in the biodigester of the biodigester plant according to the invention via at least one biomass feed.

The fermentation liquid is agitated with the help of at least one agitation means. In general, the fermentation liquid should be agitated at a speed that does not harm the microorganisms.

Examples of suitable agitation means are stirrers, in particular blade stirrers and paddle stirrers, and at least one side circuit or bypass which discharges or sucks the fermentation liquid near its surface from at least one, in particular one, outlet by means of at least one circulation pump and transports it further as a return flow through at least one return flow line to at least one preferably circular return flow distributor for the injection of the return flow into the lower region of the fermentation liquid in the reactor volume.

The fermentation or digestion of biomass takes place in the presence of elemental hydrogen.

According to the invention, the hydrogen is generated in at least one ammonia cracker by the catalytic cracking of ammonia. Preferably, the catalytic cracking of ammonia is carried out at temperatures of 300° C. to 700° C., preferably 400° C. to 650° C. and in particular 500° C. to 600° C. and at a pressure of 1.0 bar to 50 bar, preferably 1.0 bar to 40 bar and in particular 1.0 bar to 30 bar.

Examples of suitable cracking catalysts are copper nanoparticles doped with traces of ruthenium. When these are heated and simultaneously irradiated with light, the energy barrier is lowered, allowing the ammonia to be split at lower temperatures than usual (cf. http://news.rice.edu/2018/10/04/light-makes-rice-u-catalyst-more-effective-21).

Other examples of suitable cracking catalysts include nickel supported on magnesium-aluminum spinel, alumina or magnesium oxide, zirconium oxide nitride, iron oxide, manganese, platinum, palladium, lanthanum oxide, nickel-ruthenium alloys and iron oxide supported on alumina (see European patents EP 2 007 680 B1 and EP 3 028 990 B1 and U.S. patent application US 2019/0084831 A1).

Preferably, the at least one ammonium cracker is designed as a double-tube reactor in which at least one heat source is arranged in the central tube. Preferably, the at least one heat source is at least one burner that is operated with preferably hot air as oxidant and with the biogas generated in the at least one biodigester. In addition, the hydrogen-nitrogen gas mixture generated in the at least one ammonium cracker and/or the hydrogen can also be fed in. If necessary, natural gas can also be added.

Instead of or in addition to at least one open flame, resistance heaters, induction heaters, and/or hot process gases and waste gases from chemical plants and power plants can be used.

For better heat transfer to the at least one catalyst in the cracking tube (outer tube) surrounding the central tube (heating tube), a metallic packed bed with high thermal conductivity is heated with the at least one open flame of the at least one burner in the heating chamber. Preferably, packed beds made of copper are used.

The cracking tube contains at least one of the cracking catalysts described above in the form of packed beds and/or in monolithic form, as is known, for example, from catalysts for purifying engine exhaust gases. An example of such a monolithic form is the monolithic system described in the translation DE 602 21 141 T2 of the European patent specification EP 1 444 475 B1.

The at least one ammonium cracker can be arranged vertically or horizontally. If it is arranged vertically, its at least one heating chamber with the at least one burner is located at its lower end. Preferably, the at least one ammonium cracker is arranged horizontally.

Preferably, the outer diameter of the cracking tube is 5 cm to 50 cm, preferably 6 cm to 40 cm and in particular 8 cm to 30 cm. Preferably, the outer diameter of the central tube is 3 to 40 cm, preferably 3 cm to 30 cm and in particular 3 to 20 cm. The wall thickness of the tubes is preferably 1 mm to 5 mm, preferably 1.5 mm to 4 mm and in particular 2 mm to 3 mm.

Preferably, the length of the double-tube ammonia cracker is from 50 cm to 10 m, preferably from 60 cm to 8 m, and in particular from 1 m to 7 m.

Preferably, the double-tube ammonia cracker is encased in a 10 cm to 40 cm thick insulation layer for thermal insulation. Examples of suitable materials for the construction of the insulating layer are mineral fibers selected from the group consisting of aluminum silicate wool, alkaline earth silicate wool, aluminum silicate zirconium wool, high temperature glass wool, polycrystalline alumina wool, alumina ceramic fibers, mullite ceramic fibers, yttria ceramic fibers, silicon carbide, silicon carbide nitride, and silicon boride nitride carbide fibers, alkali-resistant glass fibers, quartz fibers, silica fibers, basalt fibers, boron fibers, single crystal fibers (whiskers), polycrystalline fibers, slag fibers, and nanotube fibers, and mixtures thereof.

Preferably, the pipes in which the heated ammonia and the heated air are conducted are also thermally insulated with insulation layers.

The ammonia is withdrawn in liquid and/or gaseous form from at least one pressure bottle, depending on the requirements of the at least one biodigester of the biodigester plant according to the invention. The respective flow rate is adjusted by an electronically monitored and controlled pressure reducer. The ammonia is then fed via at least one ammonia line to at least one first recuperator, wherein it is preferably heated to 300° C. to 500° C. by the hot exhaust gases discharged from the central pipe before being fed via at least one ammonia line into the cracking pipe.

The hot hydrogen-nitrogen gas mixture generated in the cracking tube contains hydrogen and nitrogen in a volume ratio of 3:1, and may contain up to 5% by volume, preferably up to 4% by volume, and in particular up to 2% by volume of unreacted ammonia. The hot gas mixture is passed through at least one hydrogen-nitrogen line to at least one second recuperator, wherein the air supplied to the burner is heated.

Preferably, the gas mixture downstream of the at least one second recuperator is cooled to preferably ≤70° C. preferably ≤65° C., particularly preferably ≤60° C. and in particular to 50 to 60° C. in a conventional and known cooling device.

Electrolysis devices powered by renewable energy can still be used to support hydrogen production by the at least one ammonia cracker.

Before the gas mixture enters the hydrogen-nitrogen distributor of the at least one biodigester, the ammonia is preferably bound by activated carbon impregnated with phosphoric acid. The resulting activated carbon/ammonium phosphate by-product is itself a product of value and can be used, for example, to produce terra preta.

In another embodiment, the cooled gas mixture is passed through sulfuric acid, in which the ammonia is bound as ammonium sulfate. The ammonium sulfate solution is also a valuable product and can be used, for example, as a liquid fertilizer.

In still another embodiment, hydrogen is separated from the cooled, ammonia-containing or ammonia-free gas mixture using a module with hydrogen-selective membranes. Examples of suitable hydrogen-selective membranes are SEPURAN® Noble membranes from Evonik, the ceramic membranes described in international patent application WO 2006/017022, page 18, line 9, to page 20, line 13, the membranes described in the article by Jinchang Zhu et al, Facile hydrogen/nitrogen separation through graphene oxide membranes supported on YSZ ceramic hollow fibers, in Journal of Membrane Science, Volume 535, 2017, pages 143 to 150, the membranes listed in German patent DE 10 2008 048 062 83, page 8, paragraph [0054], the composite membranes described in U.S. patent application US 2009/0277331 A1 in the examples 1 to 6, or the membranes described in the German disclosure document DE 23 07 853.

The ammonia-free hydrogen-nitrogen gas mixture and/or the hydrogen is or are fed at a pressure of preferably 1.0 bar to 5 bar, preferably 1.0 bar to 4 bar and in particular 1.0 bar to 3 bar into the hydrogen distributor, from where the mixture and/or the hydrogen exits or exit the hydrogen nozzles into the fermentation liquid. A part of the hydrogen can also be diverted as fuel for the ammonia cracker.

Preferably, the feed lines for the liquid and/or gaseous ammonia, the ammonia heated in the first recuperator, the air, the air heated in the second recuperator, and the biogas, as well as the discharge lines for the generated hydrogen-nitrogen mixture, are of spiral design to compensate for the mechanical stresses generated by thermal expansion and contraction.

The activated carbon masses to be used according to the invention can be produced from mineral coal, partially pyrolyzed coal, biochar, activated carbon, animal charcoal, animal waste charcoal, bone charcoal, pyrogenic carbon of different degrees of pyrolysis and lignite.

The coals can be functionalized, surface modified, pretreated, washed, soaked, soaked and dried, dried and wetted, soaked and partially dried, and/or extracted.

Furthermore, the carbons may be present as nanoparticles such as carbon nanotubes, fullerenes, graphene and/or nanocones of an average particle size of 1 nm to <1 μm, as microparticles of an average particle size of 1 μm to <1 mm and as macroparticles of an average particle size >1 mm. The average particle sizes can be measured by the skilled person with the aid of the usual and known methods which are adapted to the respective orders of magnitude.

In addition, the activated carbon mass may be in the form of magnetizable activated carbon particles as described, for example, in the German patent specification DE 10 2014 100 850 84, page 7, paragraph [0074] to page 8, paragraph [0084], and the German patent application DE 10 2014 100 849 A1.

Preferably, biochar, in particular animal charcoal, bone charcoal and/or vegetable charcoal are used. Preferably, vegetable charcoal is used. Particularly preferably, the plant charcoal has an internal surface area according to BET of at least 300 m²/g, more preferably of at least 500 m²/g and especially of at least 700 m²/g, which favors the growth of the bacteria. It has a high capillary density, which ensures particularly effective material flows and substrate supply. Particularly preferably, its pH is from 8 to 8.7, which is especially beneficial for the growth of archaea. Preferably, the H/C ratio is <0.7, preferably <0.6 and especially <0.5 according to the guideline of the European Biochar Certificate. An optimized plant carbon is described in the company publication of LUCRAT® GmbH, "Pflanzenkohle optimiert, Energy-Dezentral 2018/Eurotier".

In the production of activated carbon masses, the coals described are functionalized, surface modified, soaked and dried, dried and moistened and/or soaked and partially dried with trace elements, microelements, ultra-trace elements, ultra-microelements, bulk elements, nutrients, essential nutrients, carbohydrates, fats, proteins, minerals, vitamins, humic substances, 5-(hydroxymethyl)furfural, inorganic nitrates and/or adhesives and/or are loaded with hydrogeno-trophic and/or methanogenic archaea.

Preferably, the trace elements, ultra-trace elements, micro-elements and ultra-microelements are selected from the group consisting of lithium, rubidium, cesium, strontium, barium, chromium, cobalt, iron, fluorine, bromine, iodine, copper, manganese, molybdenum, tungsten, mercury, selenium, boron, aluminum, thallium, lead, silicon, zinc, arsenic, antimony, nickel, rubidium, tin and vanadium, and the bacteria are selected from the group of archaea.

Preferably, the trace elements, microelements, ultra-trace elements and ultra-microelements are selected from the group consisting of chromium, cobalt, iron, fluorine, iodine, copper, manganese, molybdenum, selenium, silicon, zinc, arsenic, nickel, rubidium, tin and vanadium.

Preferably, the trace elements, microelements, ultra-trace elements, ultra-microelements and/or the bulk elements are present in natural and/or synthetic minerals and/or ceramics and/or metals which are so sparingly soluble that they release the trace elements, microelements, ultra-trace elements, ultra-microelements and/or bulk elements only slowly in the sense of slow release into the fermentation liquid. An example of natural mineral is asbolan containing cobalt or limestone doped with trace elements, ultra-trace elements, microelements, and ultra-microelements.

In a particularly preferred embodiment, the trace elements, microelements, ultra-trace elements, ultra-microelements and/or bulk elements are present in the form of their complexes.

Preferably, the complexing agents are selected from the group consisting of bidentate, tridentate, tetradentate and pentadentate ligands and higher dentate ligands such as crown ethers and nitrogen analogues. In particular, the complexing groups contain boron atoms, oxygen atoms, nitrogen atoms, phosphorus atoms, sulfur atoms and/or selenium atoms.

Very preferably, the complexing agents are selected from the group consisting of lignin, starch, polysaccharides, amino acids, polyvinyl alcohols, polyglycols, polyethyleneimines, acetylacetone, ethylenediamine, diethylenetriamine, iminodiacetate, triethylenetetramine, triaminotriethylamine, NTA nitrilotriacetic acid, bis(salicylidene)ethylenediamine, 1,4,7,10-tetraazacyclododecane-1,4,7,10-tetraacetate, oxalate, citrate, dimethylglyoxime, 8-hydroxyquinoline, 2,2'-bipyridine, 1,10-phenanthroline, dimercaptosuccinic acid, 1,2-bis(diphenylphosphino)ethane, 2-(2-aminoethylamino)ethanol, ethylenediamine triacetate, EDTA ethylenediamine tetraacetate, EGTA (ethylene glycol-bis(aminoethyl ether)-N,N,N',N'-tetraacetic acid), DOTA (1,4,7,10-tetraazacyclododecane-1,4,7,10-tetraacetic acid), NTA (nitrilotriacetic acid), EDDS (ethylenediaminedisuccinic acid), D-penicillamine, deferoxamine, citric acid, polycarboxylates, zeolites, phosphonates, triethanolamine, gluconates, alaninediacetic acid sodium salt (ADA), methylglycinediacetic acid (MGDA), diethylenetriaminepentaacetic acid (DTPA), propylenediaminetetraacetic acid (PDTA), isoascorbic acid (E315), sodium isoascorbate (E316), citric acid (E330), sodium citrate (E331), potassium citrate (E332), calcium nitrate (E333), tartaric acid (E334), sodium tartrates (E335), potassium tartrates (E336), sodium potassium tartrates (E337), sodium phosphates (E339), potassium phosphates (E340), calcium phosphates (E341), calcium tartrate (E354), triammonium citrate (E380), calcium EDTA (E385), polyoxyethylene sorbitan monolaurate (polysorbate 20) (E432), polyoxyethylene sorbitan monooleate (polysorbate 80) (E433), polyoxyethylene sorbitan monopalmitate (polysorbate 40) (E434), polyoxyethylene sorbitan monostearate (polysorbate 60) (E435), polyoxyethylene sorbitan tristearate (polysorbalt 65) (E436), beta-cyclodextrin (E459), diphosphates (E450), triphosphates (E451), polyphosphates (E452), gluconic acid (E574), sodium gluconate (E576), potassium gluconate (E577), calcium gluconate (E578), ferrous II gluconate (E579), phytates, bentonite, zeolites and montmorillonite.

The activated carbon masses may be fixed

In one embodiment, the fixed activated carbon masses may be present as at least one layer fixed with the aid of at least one adhesive. The at least one adhesive may form a separate layer or be present in admixture with the fixed, activated carbon mass.

Suitable adhesives can be selected from the group consisting of biopolymers, polysaccharides, chemically curing adhesives, polymerization adhesives, cyanoacrylate adhesives (instant adhesives), methyl methacrylate adhesives, anaerobic curing adhesives, unsaturated polyesters (UP resins), radiation curing adhesives, polycondensation adhesives, phenol-formaldehyde resin adhesives, silicone-silane crosslinked polymer adhesives, lignin adhesives, polyimide adhesives, polysulfide adhesives, polyaddition adhesives, expoxy resin adhesives, polyurethane adhesives, silicone polyisocyanate adhesives, physically setting adhesives, solvent based adhesives, contact adhesives, dispersion adhesives, cement, cement-based adhesives, foamed concrete, gypsum-based adhesives, plastisols, adhesives without a setting mechanism and slaked lime and adhesives based thereon.

The foregoing adhesives may have partially open structures, they may be held together by point bonds, they may be encapsulated, partially encapsulated, non-encapsulated, bonded to a background, and/or have a backbone. They may also have curing agents and/or flow agents added.

The above adhesives for the carbon nanoparticles, carbon microparticles and/or carbon macroparticles, which are functionalized, surface-modified, soaked, soaked and dried, dried, dried and moistened, and soaked and partially dried, are listed only by way of example and are not exhaustive. Accordingly, the list is intended to illustrate the variety of possibilities, and the person skilled in the art can readily indicate further possibilities on the basis of his general technical knowledge.

Preferably, biodegradable and/or organic adhesives are used.

Activated carbon masses fixed in this way can be used, for example, to coat the walls of the biodigester, as described in the German patent application DE 10 2015 012 436 A1.

Further, the fixed, activated carbon masses may be enclosed in immobile, fluid-permeable containers. Examples of suitable containers include bags, pouches, sacks, buckets, cans, boxes, envelopes, and cartons made of paper, paperlike materials, textile, metal, and/or any combinations thereof. Furthermore, freezer bags, pressure seal bags, trash bags, general purpose bags, cloth bags, shopping nets, air permeable bags for food storage, and vacuum cleaner bags may be considered. Also, valve bags, cross-bottom bags, block-bottom bags, pinch bags, flat bags, pleated bags, and/or nets can be used. It is essential that these containers are permeable to the fermentation liquid but do not release electrically conductive particles into the reactor volume.

The containers can be placed in the biodigester according to the invention in different ways. For example, they can be placed on the bottom, on the side walls, in front of the side walls, in the middle of the biodigester and/or on the stirrers, and/or on and/or in systems such as support materials like curtains, grids, woods and/or in other arbitrary bodies.

In a further embodiment, the biodigester plant according to the invention contains at least one, preferably at least two, more preferably at least three, particularly preferably at least four and especially at least five suspended bodies or floats, which carry the activated and preferably fixed carbon masses, in the fermentation liquid.

The floats are freely movable in the fermentation liquid or anchored to the surface of the reactor bottom, lid, roof or cover, preferably to the surface of the reactor bottom, of the biodigester.

The float to be used according to the invention comprises at least one buoyancy body, at least one fixed activated carbon mass and at least one weight.

The at least one fixed activated carbon mass and the at least one weight are balanced such that the buoyancy body preferably suspends the float in the fermentation liquid vertically or substantially vertically.

In the context of the present invention, the term "in suspension" includes the case where the buoyancy body of the float is partially or completely submerged in the fermentation liquid or floats on the surface of the fermentation liquid.

The size and weight of the float can vary very broadly and can therefore be excellently adapted to the design specifics of a given biodigester plant according to the invention and the requirements of a given digestion process according to the invention.

Preferably, the total length of the float. i.e. the distance from its weight to the highest point of the float, is 10 to 100 cm.

Preferably, the weight of the float is 10 to 1000 g.

The floats to be used in accordance with the invention can be of a wide variety of shapes and sizes. What is essential is that their buoyancy is sufficient to keep the float in suspension. The necessary buoyancy can be determined by calculation or with the aid of a few simple experiments.

The buoyancy bodies can be hollow bodies, solid bodies or sponge-like bodies. It is essential that they do not decompose in the fermentation liquid They can have any three-dimensional shape. Examples of suitable shapes are platonic bodies such as spheres, pyramids, cylinders, octahedra, dodecahedra or icosahedra. Furthermore, hemispheres or rings are possible. Their size depends on the weight of the fixed, activated carbon masses which they should keep in suspension. Suitable materials for the buoyancy bodies are plastics, wood, light metals or glass. Preferably, plastics are used for hollow bodies. For solid bodies, plastics or wood are preferably used.

Examples of suitable polymers that are stable to the fermentation liquid are polyolefins such as polyethylene, polypropylene, polybutadiene, polyisoprene and their copolymers, polyvinylaromatics such as polystyrene, poly(alpha-methylstyrene) and their copolymers, poly(meth)acrylates, polyesters, polyethers, polyamides, polyesterimides, polyketones, polyetherketones or polysulfones. The person skilled in the art can easily select other suitable polymers based on his general knowledge of the subject. It is further advantageous if the polymers are three-dimensionally crosslinked. Still another advantage results if the polymers are biodegradable.

The hollow bodies can be filled with air, nitrogen or helium. Preferably, air is used. However, they can also be evacuated. The hollow bodies can also contain spots in their walls that are dissolved by the fermentation liquid over time, so that they gradually or rapidly fill with the fermentation liquid, causing the floats to sink to the bottom of the reactor. This can also be done in a controlled manner by having valves built into the wall that can be opened by radio remote control. The floats that have sunk to the bottom of the reactor can then be disposed of in a simple manner.

The buoyancy bodies can be manufactured in a wide variety of ways. For the production of solid buoyancy bodies, for example, ablative processes such as machining, cutting, grinding or milling can be considered. For the production of hollow bodies, build-up processes such as injection molding or 3-D printing can be considered.

The float to be used according to the invention comprises at least one fixed, activated carbon mass. For special applications, several, for example 2 to 30, fixed, activated carbon masses can also be used.

The amount of fixed activated carbon mass is selected to be held in suspension together with the weight or, if the float is anchored to the reactor floor, by the at least one float alone.

In one embodiment, the fixed activated carbon mass may be present as at least one layer fixed with the aid of at least one adhesive. The at least one adhesive may form a separate layer or may be present in admixture with the fixed, activated carbon mass.

Suitable adhesives can be selected from the group consisting of biopolymers, polysaccharides, chemically curing adhesives, polymerization adhesives, cyanoacrylate adhesives (instant adhesives), methyl methacrylate adhesives, anaerobic curing adhesives, unsaturated polyesters (UP resins), radiation curing adhesives, polycondensation adhesives, phenol-formaldehyde resin adhesives, silicone-silane crosslinked polymer adhesives, lignin adhesives, polyimide adhesives, polysulfide adhesives, polyaddition adhesives, expoxy resin adhesives, polyurethane adhesives, silicone polyisocyanate adhesives, physically setting adhesives, solvent based adhesives, contact adhesives, dispersion adhesives, cement, cement-based adhesives, foamed concrete, gypsum-based adhesives, plastisols, adhesives without a setting mechanism and slaked lime and adhesives based thereon.

The foregoing adhesives may have partially open structures, they may be held together by point bonds, they may be encapsulated, partially encapsulated, non-encapsulated, bonded to a background, and/or have a backbone. They may also have curing agents and/or flow agents added.

The above adhesives for the carbon nanoparticles, carbon microparticles and/or carbon macroparticles, which are functionalized, surface-modified, soaked, soaked and dried, dried, dried and moistened, and soaked and partially dried, are listed only by way of example and are not exhaustive. Accordingly, the list is intended to illustrate the variety of possibilities, and the person skilled in the art can readily specify further possibilities on the basis of his general technical knowledge.

Biodegradable and/or organic adhesives are preferred.

In one embodiment, the activated carbon mass fixed with the aid of adhesives may be fixed to the surface of the buoyancy bodies and/or the weights.

The weights themselves are preferably solids that have a higher density than the fermentation liquid. Examples of suitable weights are natural and synthetic minerals, synthetic and natural ceramics, glass and metals. They can have a wide variety of three-dimensional shapes and can therefore be excellently adapted to the particular float. Examples of suitable three-dimensional shapes are given above with the floats.

In special cases, the dead weight of the fixed, activated carbon mass can take over the function of the weight.

The activated coal masses described above are also fixed by placing them in containers held in suspension by the buoyancy bodies and the weights.

It is essential for the container to be semi-permeable so that the fermentation liquid can come into contact with the fixed, activated carbon mass.

The materials for the containers must be mechanically stable and must not be attacked by the fermentation liquid, Examples of suitable materials are the polymers, metals or glass listed above. The shape of the containers depends primarily on the spatial requirements of the fermentation reactor and the requirements of the digestion process carried out with the aid of the fermentation reactor. For example, the containers may be in the form of stockings, bags, tubes, or boxes, which may be provided with perforations. The containers themselves may in turn be divided into at least two compartments.

In the context of the present invention, "through holes" are understood to mean openings of any outline and size. Thus, they may have a round, triangular, square, hexagonal, star-shaped and/or slot-shaped outline. The clear width can also vary widely and can therefore be excellently adapted to the requirements of the individual case. For example, the clear width can be in the order of 1 nm to 5 mm. It is essential that the clear width does not become so large that parts of the fixed, activated carbon mass lose their hold on the total mass and enter the fermentation liquid.

In a particularly advantageous embodiment, the containers are in the form of stockings made of a permeable woven or knitted fabric. Very particularly preferred are stockings made of glass fabric.

Preferably, the containers can be emptied and refilled with fresh, fixed, activated carbon mass. Closable filling openings can be provided for this purpose. The closing devices may be flanges and matching insertion channels, hose clamps, threads or closing caps.

To prevent the floats from getting caught on moving devices of the biodigester and from damaging the devices and the floats, or to prevent the floats from clogging the inlets and outlets of the biodigester, it is advantageous for the float(s) to be located behind a protective grid or net. This protective grid still allows the floats to move freely within the fenced area, but it prevents the floats from entering the critical areas of the biodigester.

It is also possible that the buoyancy bodies are connected to each other, for example, with threads, wires or chains to form bandages.

The above-described fixed, activated coal masses are described in detail in German patent specification 10 2016 004 026 B4, page 4, paragraph [0034], to page 7, paragraph [0080], page 9, paragraph [0087], to page 11, paragraph [0122], in conjunction with FIGS. 1 to 11.

In a further advantageous embodiment, the activated carbon masses are in the form of powders of an average particle size >1 mm, pressed pellets, pressed rods or pressed rings in the floats which float on and/or on the surface of the fermentation liquid. Preferably, these floats are made by injection molding from the polymers described above. Preferably, they comprise a lid that is removably connected to the can that holds the activated carbon masses. For example, the lid may be connected to the can by tongue-and-groove joints. The walls of the floats have flow-through openings that allow hydrogen and/or a hydrogen-nitrogen mixture to enter, fermentation liquid to drain, and biogas to exit.

The floats can be of any desired shape such as hollow cylinders that float vertically in the liquid, hollow cones that float with the tip down, or plate-shaped floats whose height is less than their horizontal diameter. The plate-shaped floats can have any desired outline. For example, they may be triangular, quadrangular, pentagonal, hexagonal, or octagonal. The top, side walls, and/or bottom of the floats may be rectilinear and flat or convexly curved. The corners of the floats may also be rounded. It is advantageous if the floats are not able to combine into a closed parquet-like structure on the surface, but that there are openings between them to facilitate the escape of the biogas.

In a further advantageous embodiment, the activated carbon masses are encased in fluid-permeable spherical containers preferably of a diameter of 0.5 cm to 5 cm. The fluid-permeable spherical containers are composed of at least one of the polymers described above containing fillers of a density >1 g/cm³. These fluidized bodies can advantageously be agitated in a fluidized bed in the fermentation liquid, thus creating a particularly high contact area. When the agitation means are switched off, the fluidized beds sink to the sieve trays of the fluidized bed reactors, whereupon they can be stirred up again.

In still another preferred embodiment, the activated carbon masses are fixed on and/or in at least one, in particular one, fixed bed. Any materials can be used as a support for the fixed bed, as long as they are not attacked by the fermentation liquid. However, the fixed bed can also be composed of pressed pellets, balls, rings and rods of the activated coal masses. The at least one fixed bed is preferably located in at least one, in particular one fixed bed reactor, which is located in at least one, in particular one, run-up side circuit of the at least one two-stage biodigester. In this case, the fermentation liquid is sucked out of the at least one first-stage biodigester at its bottom and is passed as an overflow stream through the at least one fixed-bed reactor and is reintroduced from its upper end into the at least one first-stage biodigester from above.

In still another preferred embodiment, powdered activated carbon masses, in particular activated carbon microparticles suspended in the fermentation liquid, are used.

In an alternative embodiment of the biodigester plant according to the invention, the biodigester plant comprises at least one device for treating activated coal masses, preferably powdered activated coal masses and in particular activated carbon microparticles, with hydrogen at higher pressure with at least one pressure line and at least one spray lance for injecting the hydrogen-containing activated coal masses as spray cones into the fermentation liquid of the at least one biodigester.

In still another preferred embodiment of the biodigester plant according to the invention, the 1st phase: hydrolysis, the 2nd phase: acidogenesis or acidifying phase and the 3rd phase: acidogenesis or vinegar forming phase are carried out in at least one first biodigester. The fermentation liquid in the reactor volume has a pH <7.

The 4th phase: methanogenesis is carried out in at least a second biodigester. The fermentation liquid in the reactor volume has a pH >7.

Preferably, the biodigester plant according to the invention also comprises at least one secondary fermenter for completing methanogenesis. The digested fermentation liquids can thereby be conveyed from bottom chamber to bottom chamber. The gas spaces of the above-mentioned at least two or at least three biodigesters are connected to each other via gas lines.

In a preferred embodiment, the fermentation products are fed into a solid-liquid separator. The solid fermentation products are discharged via a solids discharge and brought to further use as fertilizer or for the production of terra preta. The liquid fermentation products can be used as liquid fertilizer or they can be recycled to at least one biodigester.

In still another preferred embodiment, gaseous biomass can additionally be fed to the fermentation liquid of the at least one biodigester. Examples of suitable gaseous biomasses are landfill gases, sewage gases, digester gases and sump gases.

In still another preferred embodiment, carbon dioxide from other carbon dioxide sources can be fed to the fermentation liquids, particularly in the 4th phase: methanogenesis. In addition to pressurized cylinders, carbon dioxide-containing exhaust gases from incinerators, combustion engines, cement kilns and lime kilns are particularly suitable. Their thermal energy can be used to heat the fermentation liquid and the at least one ammonia cracker. This further preferred embodiment is ideally suited for sequestering carbon dioxide, so that the biodigester plant in question according to the invention is not only carbon dioxide-neutral, but even serves as a carbon dioxide sink.

For the biodigester plant according to the invention described above, it is essential that the ammonia is produced with the aid of renewable energies and that the at least one ammonia cracker is operated with the aid of renewable energies.

Renewable energy can be solar energy, bioenergy from biomass in various forms, hydropower, wind energy and geothermal energy.

Preferably, the solar energy is produced with photovoltaic, solar thermal, solar chemical and updraft power plants, the bioenergy is produced with biomass in various forms, namely with vegetable oil, wood, biodiesel, bioethanol, cellulose-ethanol, biogas, BtL (biomass-to-liquid) fuels and biohydrogen, hydropower is generated with dams and barrages, run-of-river power plants, watermills, power buoys, ocean wave energy, ocean current energy, and ocean heat, and wind energy is generated by wind turbines, airborne wind turbines, and windmills.

It is essential for the biodigester plant and process according to the invention that the fermentation liquid and, if applicable, the activated biochar mass contain hydrogenotrophic microorganisms and anaerobic microorganisms, in particular archaea.

Examples of suitable hydrogenotrophic archaea include *Methanosoete* spp. and *Metanosarcina* spp. Further examples are disclosed by the international patent application WO 2011/003081, page 25, paragraph [0099]. *Methanothermobacter Thermautotropicus* lines and variants are disclosed by the European patent EP 2 661 511 B1.

Examples of suitable methanogenic archaea include *Chlostridium* spp, *Selenomonas* spp, *Acelobacternum* spp, *Pelobacter* spp, *Butyrobacterium* spp, *Eubacterium* spp. *Laczobacillus* spp, *Riminococus* spp, *Streptococcus* spp, *Propionibacterium* spp, *Butyrivibrio* spp, and *Acetivibrio* spp. Further examples are given in Tables 2 and 3 of the international patent application WO 2011/003081.

The at least one biodigester is used to carry out the digestion process or fermentation process according to the invention. With the aid of carbon in the form of the activated carbon masses described above, the said process promotes the growth of useful microorganisms and/or the increase in metabolism and/or catabolism and/or anabolism and/or increases the yield of biogas without loss or virtually without loss with respect to the carbon mass. Electrolysis and the use of hydrogenotrophic methanogenic microorganisms and archaea increase the yield of biogas beyond what was previously known.

The digestion process according to the invention is preferably carried out at temperatures of 45° C. to 100° C., preferably 50° C. to 80° C. and in particular 50° C. to 75° C. Preferably, the pressure in the biodigester according to the invention is >1.0 bar, preferably >2 bar and in particular >3 bar. In general, the pressure should not exceed 30.0 bar for safety reasons. Particularly preferably, the digestion process according to the invention is carried out at a pH of 5.5 to 8.5 and preferably 6 to 7.5.

It is particularly advantageous that the digested biomasses or fermentation products produced by the digestion process according to the invention and/or the activated coal masses used in the process can be excellently used as fertilizers and/or for the production of terra preta.

If the magnetizable activated carbon particles described above are used, drained digested biomass with the magnetizable activated carbon particles is passed via at least one drain into at least one magnetic separator, preferably into at least one magnetic separator according to German patent application DE 10 2014 100 849 A1, wherein the particles are retained. The digested biomass freed from the particles may be discharged from the at least one magnetic separator via at least one drain. If necessary, a portion of the digested biomass freed from the particles can be pumped back into the at least one reactor volume via at least one return line with the aid of at least one feed pump. As soon as the at least one magnetic separator has reached its capacity limit, which can be determined by magnetic measurements on the at least effluent from the at least one magnetic separator, the at least one effluent from the at least one biodigester is closed and the particles can be removed from the magnetic separator with the aid of suitable devices, optionally reactivated, i.e. dried and mixed with methanogenic and hydrogenotrophic archaea and with preferably up to 1.0 wt. % of inorganic nitrates, trace elements, ultra-trace elements, microelements, ultra-microelements and bulk elements as well as nutrients, essential nutrients, carbohydrates, fats, proteins, minerals and vitamins, and returned to the biodigester BK.

The embodiments described below are given only by way of example and are not exhaustive. The person skilled in the art can indicate further possibilities on the basis of his general knowledge without any inventive activity of his own. It therefore goes without saying that the features mentioned above and explained in more detail below can be used not only in the combinations and configurations indicated, but also in other combinations and configurations or on their own, without departing from the scope of the present invention.

BRIEF DESCRIPTION OF THE FIGURES

The invention will now be explained in more detail by means of the embodiments, with reference to the attached FIGS. 1 to 4. They show in simplified, not to scale representation:

FIG. 2a the top view of the longitudinal section through a liquid-permeable float SCH in the fermentation liquid GF with pellets PK of activated carbon masses K;

In FIGS. 1 to 4, the reference signs have the following meaning:

Figure 1:
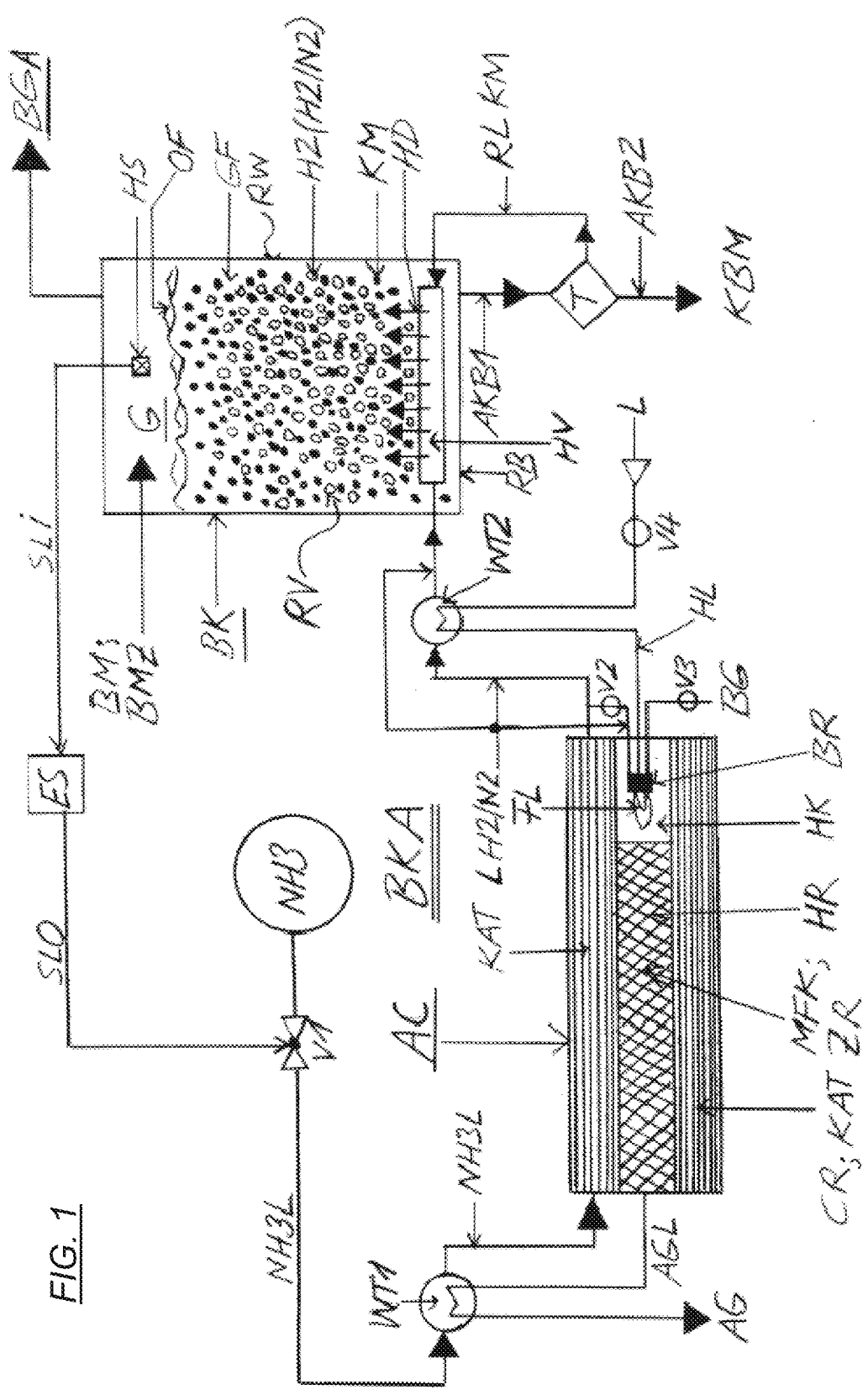
FIG. 1 the top view of a schematic diagram of a biodigester plant BKA according to the invention with an ammonia cracker AC and a biodigester BK.
Figure 3:
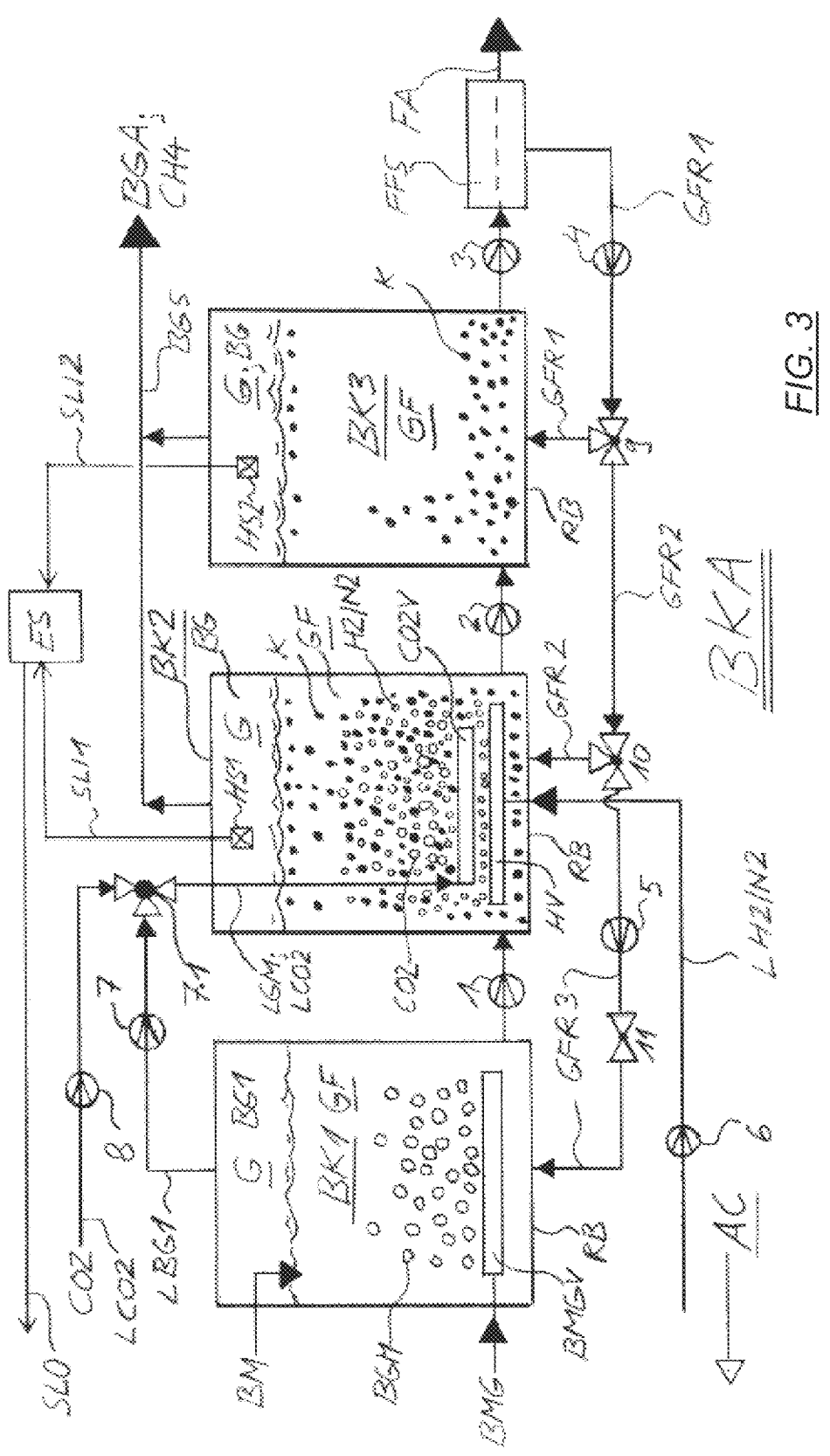
FIG. 3 the top view of a schematic representation of a further embodiment of the biodigester plant BKA according to the invention with a biodigester BK1 for hydrolysis, acidogenesis and acetogenesis, a biodigester BK2 for methanogenesis and a biodigester BK for postfermentation.

AC Ammonia cracker
AG Exhaust gas from the heating pipe HR
AGL Exhaust line
AKB1 Drain for magnetic, activated carbon particles KM containing digested biomasses and fermentation products BM
AKB2 Flow for digested biomasses and fermentation products freed from magnetic activated carbon particles KM KBM
BG Biogas; Methane
BG1 Methane/carbon dioxide mixture
BGA Biogas drainage
BGS Biogas collection line
BGZ Biomass feed for gaseous biomass BMG

17

18

BK Biodigester

BK1 Biodigester for the hydrolysis, acidogenesis and acetogenesis; pH of fermentation liquid GF <7

BK2 Biodigester for methanogenesis; pH of fermentation liquid GF >7

BK3 Secondary fermenter

BM Biomass, liquid-solid

BMG Biomass, gaseous

BMGV Distributor for gaseous biomass BMG

BMZ Biomass feed

BR Burner

CH4 Methane

CO2 Carbon dioxide

CO2V Carbon dioxide distributor

CR Crack pipe

DE Lid of the float SCH

DO Can of the float SCH

ES Electronic data processing system for electronic control of the biodigester plant BKA FA Solids discharger for the solid fermentation products BM FFS Liquid-solid separator for the fermentation products BM FL Flame FNV Circumferential spring-groove connection G Gas compartment GF Fermenting liquid; fermentation liquid GFR1 Recirculation for the liquid fermentation products BM from the liquid-solid separator FFS to BK3

GFR2 Recirculation for liquid fermentation products BM from liquid-solid separator FFS to BK2 via GFR1

GFR3 Recirculation for the liquid fermentation products BM from the liquid-solid separator FFS to BK1 via GFR1 and GFR2

H2 Hydrogen

H2K Hydrogen-containing activated carbon mass K

H2KM Hydrogen-containing activated magnetic carbon KM

H2/N2 Hydrogen-nitrogen mixture

HD Hydrogen nozzle, hydrogen-nitrogen nozzle

HK Heating chamber

HL Hot air line

HR Heating pipe

HS Hydrogen sensor

HV Hydrogen distributor, hydrogen-nitrogen distributor

K Activated coal mass

KAT Crack catalyst

KBM Digested biomass or fermentation products BM

KM Magnetizable carbon mass, magnetizable activated carbon mass, filter cake, magnetizable activated carbon particles.

L Air

LAN2 Nitrogen outlet line

LCO2 Carbon dioxide line

LGM Gas mixture line,

LH2 Line for hydrogen H2

LH2/N2 Line for hydrogen-nitrogen mixture H2/N2

LK Line for powdered, activated carbon masses K

LN2 Nitrogen purge line

MFK Metallic packed bed, heat exchanger

N2 Nitrogen

NH3 Ammonia

NH3L Ammonia line

O Opening

OF Surface of the moving fermentation liquid GF

PK Pellets from activated carbon mass K

RB Reactor bottom

RL Return line

RV Reactor volume

RW Reactor wall

SCH Float

SLI Input signal line from HS to ES

SLI1 Input signal line from HS1 to ES

SLI2 Input signal line from HS2 to ES

SLO Output signal line

T Magnetic separator

V1 Electronically controlled pressure reducer and flow valve

V2 Electronically controlled flow valve for hydrogen H2 or for hydrogen-nitrogen mixtures H2/N2

V3 Electronically controlled flow valve for biogas

V4 Electronically controlled flow valve for the supply of air L

VBK Device for the treatment of activated coal masses K with hydrogen H2 at higher pressure WT1 Heat exchanger (recuperator) for heating ammonia NH3 and cooling exhaust gas AG WT2 Heat exchanger (recuperator) for heating air L and cooling hydrogen H2 or hydrogen-nitrogen mixture H2/N2

ZR Central pipe

→ Direction of flow and/or transport of liquid, solid and/or gaseous substances and substance mixtures 1 Thick matter pump for conveying the liquid BM fermentation products from BK1 to BK2

2 Thick matter pump for conveying the BM liquid fermentation products from BK2 to BK3

3 Thick matter pump for conveying BM liquid fermentation products from BK3 to FFS 4 Thick matter pump for recirculation of BM liquid fermentation products from FFS to BK3 and BK2

5 Thick matter pump for recirculation of BM liquid fermentation products from FFS to BK1

6 Injector for H2/N2 or H2

7 Injector for BG1

7.1 Electronically controlled three-way valve

8 Carbon dioxide injector

9; 10 Electronically controlled three-way valves

11 Electronically controlled outlet valve

12 Pressure vessel 12.1 Tubular upper section 12.2 Tapered lower section 12.3 Removable, pressure- and vacuum-tight lid 13 Shut-off valve for vacuum and overpressure 14 Pass valve for hydrogen H2 or hydrogen/nitrogen mixture H2/N2

15 Pass valve for activated carbon mass containing hydrogen H2/K; H2/KM

16 Outlet valve for powdered, activated carbon masses K; KM

17 Pass valve for nitrogen N2

18 Dosing unit for powdered, activated carbon masses K; KM; Rotary feeder

19 Manometer

20 Safety valve, pressure maintaining valve

21 Sieve; strainer

22 Vacuum pump

23 Blind flange

24 Three-way valve

25 Pressure line for hydrogen-containing, powdered, activated carbon masses K

26 Check valve; throttle check valve

27 Sealed feedthrough of pressure line 25 through reactor wall RW

28 Spray lance

29 Spray cones of hydrogen H2 and hydrogen-containing powdered activated carbon masses H2K; H2KM.

30 Swirl in the fermentation liquid GF of the biodigester BK

31 Spray lance for hydrogen H2 or hydrogen/nitrogen mixture H2/N2

32 Spray cone

33 Compressor

34 Centrifugal separator; cyclone

35 Solids discharge

DETAILED DESCRIPTION OF THE FIGURES

Manufacturing Example 1

The Production of Activated Carbon Mass K

The activated charcoal masses K used in the following were prepared from beech charcoal of an internal surface area according to BET of 800 m$^2$/g, a high capillary density and a pH of 8 to 8.7. The beech charcoal was loaded with methanogenic and hydrogenotrophic archaea and with 1 wt % of inorganic nitrates, trace elements, ultra-trace elements, microelements, ultra-microelements and bulk elements, as well as nutrients, essential nutrients, carbohydrates, fats, proteins, minerals and vitamins, resulting in the activated charcoal mass K.

The carbon mass K was advantageously used as pellets PK in the floats SCH according to FIG. 2 described below. Nutrients for the microorganisms could still be added to the fermentation liquids GF described below via feed lines, which were not shown for the sake of simplicity.

Manufacturing Example 2

The Preparation o him f Magnetizable Activated Carbon Particles KM.

The magnetizable activated carbon particles KM were prepared following Example 2 of the German patent DE 10 2014 100 850 B4, page 8, paragraph [0082]. For this purpose, 55.5 kg of industrially produced microcrystalline cellulose was charged together with 600 l of deionized water in a 1000-liter HTC reactor. For the hydrothermal reaction with oxidic ferrites, 33.4 kg of manganese-zinc-ferrite powder of a particle size of 30 to 80 μm were added. The mixture was stirred slowly to prevent blockage of the stirrer. A temperature of 250° C. and a reaction time of 20 hours with a heating rate of 5° C./minute were selected as the reaction conditions. The reaction temperature was controlled with a PID temperature controller. The accuracy of the controller was set to ±1.0 degree Celsius. The pressure was not controlled but was recorded during the reaction. The mixture was stirred continuously throughout the hydrothermal treatment at 90 rpm. After the reaction was complete, the heating system was turned off and the reactor was allowed to cool. Generally, it took 15 hours for the reactor to cool from 250° C. to 25° C. while the pressure dropped from 45 bar to 5.0 bar. The gaseous byproduct was drained and the solid magnetizable carbon mass KM was filtered off. The resulting filter cakes KM were crushed, dried and loaded with methanogenic and hydrogenotrophic archaea and with 1 wt % of inorganic nitrates, trace elements, ultra-trace elements, microelements, ultra-microelements and bulk elements, as well as nutrients, essential nutrients, carbohydrates, fats, proteins, minerals and vitamins, resulting in magnetizable activated carbon particles KM.

Manufacturing Example 3

The hydrogen H2 used for the production of ammonia was produced by the electrolysis of water. The electricity required for this was supplied by appropriately dimensioned photovoltaic systems. The Haber-Bosch process was used to produce the ammonia from nitrogen N2 and hydrogen H2. The thermal and electrical energies required for the plants were supplied by updraft power plants. Thus, only renewable energy was used in the production of ammonia.

FIG. 1

1. Carbon Dioxide-Neutral Biodigester Plant BKA for a Single-Stage Digestion Process.

1.1 The Biodigester BK

The biodigester BK was of common and known construction and was designed for a capacity of 75 kW$_{el}$ and an annual yield of 643,000 kWh of electricity.

The fermentation liquid GF contained cattle manure and shredded corn silage as biomass BM, two species of methanogenic microorganisms (e.g. *Methanosaeta* spp. and *Methanosarcina* spp), and two species of hydrogenotrophic microorganisms (e.g. *Methanothermobacter thermautotropicus* and *Methanobacterium formicium*). The biomass BM was introduced into the biodigester BK via the biomass feed BMZ. The fermentation liquid GF was stirred with a paddle stirrer (not shown) driven by an explosion-proof electric motor in such a way that the fermentation was not disturbed.

The fermentation liquid GF further contained floats SCH according to FIG. 2, which floated on the fermentation liquid GF, and dispersed, magnetizable, activated carbon particles KM according to the Manufacturing Example 2. The fermentation liquid GF filled the reactor volume RV to about 4/5. Above its surface was the gas space G, in which the biogas BG accumulated. In the gas space G there was also a hydrogen sensor HS for determining the hydrogen concentration in the gas phase. The determined value of the hydrogen concentration served as a control variable for the productivity of the ammonia cracker AC, For this purpose, the measured signal was fed via the input signal line SLI to an electronic data processing system to the electronic control system ES, where it was processed. The data processing equipment then gave a control signal via the output line SLO to the electronically controlled actuator of the electronically controlled pressure reducer and flow valve V1 of the ammonia supply NH3, which regulated the amount of ammonia supplied to the ammonia cracker AC. A concentration of 2 to 3% by volume of hydrogen H2 in the gas space G was considered advantageous, because this increased the calorific value of the biogas BG.

The biogas BG produced by fermentation from methane and small amounts of hydrogen, which increased the calorific value, were discharged through the outlet pipe BGA. The content of hydrogen sulfide, carbon dioxide, carbon monoxide, ammonia and oxygen in the biogas BG was below the respective detection limits. Therefore, the methane content of >90 vol % of the biogas had the methane content required by DVGW G 262 (German Technical and Scientific Association for Gas and Water) for feeding into the L-gas network.

The hydrogen H2 was introduced into the fermentation liquid GF in the form of fine gas bubbles via an annular hydrogen distributor HV with hydrogen nozzles HD, which was arranged horizontally above the reactor bottom RB In the fermentation liquid GF, the hydrogen H2 was digested during fermentation and, in particular, converted the resulting carbon dioxide into methane according to equation 1:

$$CO_2 + 8H_2 = CH_4 + 2H_2O \qquad (1).$$

The digested biomass KBM was discharged continuously or discontinuously together with the magnetizable activated coal particles KM via the effluent AKB1. New biomass BM was continuously or discontinuously fed via the biomass feed BMZ. In addition, any losses of magnetizable activated carbon particles KM that may have occurred were compensated for by adding fresh particles KM to the fermentation liquid GF using a powder feeder (not shown).

The drained digested biomass KBM with the magnetizable activated coal particles KM was fed via the drain AKB1 into a magnetic separator T according to the German patent application DE 10 2014 100 849 A1, wherein the particles KM were retained. The digested biomass KBM, freed from the particles KM, was discharged from the magnetic separator T via the outlet AKB2, if necessary, part of the digested biomass KBM freed from the particles KM was pumped back into the reactor volume RV via the return line RL with the aid of a feed pump (not shown). As soon as the magnetic separator T reached its capacity limit, which could be determined by magnetic measurements on the effluent AKB2, the effluent AKB1 was closed, and the particles KM were removed from the magnetic separator T with the aid of suitable devices (not shown), reactivated if necessary, i.e. dried and treated with methanogenic and hydrogenotrophic archaea and with 1 wt. % of inorganic nitrates, trace elements, ultra-trace elements, microelements, ultra-microelements and bulk elements, as well as nutrients, essential nutrients, carbohydrates, fats, proteins, minerals and vitamins, and returned to the biodigester BK.

1.2 The Hydrogen Production

The production of hydrogen H2 as a hydrogen-nitrogen mixture H2/N2 was based on the process described in European patent EP 3 028 990 81, page 8, FIG. 1, in conjunction with pages 4 and 5, paragraphs [0025] to [0029].

The components of the ammonia cracker (AC) for the production of hydrogen H2 were constructed of corrosion-resistant, thermostable and pressure-resistant V4A steel, so that the ammonia cracker (AC) could be operated at temperatures of up to 700° C. and pressures of up to 30 bar.

Ammonia was fed from the ammonia supply NH3 to the recuperator WT1 via the ammonia line NH3L at a flow rate and pressure regulated as required by the pressure reducer V1 controlled by the electronic data processing system ES The biodigester's demand for hydrogen H2 was determined by the hydrogen sensor HS; as soon as the hydrogen concentration in the gas space G fell below the detection limit of the hydrogen sensor HS, the sensor HS sent a signal to the data processing system ES via the input signal line SLI, which in turn sent a control signal to the actuator of the pressure reducer V1 to open via the output signal line SLI. If the concentration of hydrogen H2 in the gas chamber G exceeded 4% by volume, the command to close the pressure reducer V1 was sent in the same way.

In the WT1 recuperator, the ammonia was heated to 450° C. by the hot exhaust gas AG discharged from the HR heating tube or the central tube ZR of the horizontally arranged ammonia cracker AC via the AGL exhaust lines. The heating tube HR; ZR was arranged centrally in the ammonia cracker AC and contained a metallic packed bed MFK made of copper, which was heated with the aid of the flame FL of the burner BR and transferred the heat energy to the cracking catalyst KAT, which was located in the outer tube or cracking tube CR concentrically surrounding the heating tube ZR; HR. Nickel supported on alumina was used as the cracking catalyst KAT. Its temperature was 600° C. The ammonia cracker AC was thermally insulated by a 30 cm thick layer (not shown) of high temperature glass wool.

The hot ammonia flowed through the cracking catalyst KAT and was split at 600° C. into hydrogen H2 and nitrogen. The resulting gas mixture H2/N2 contained the hydrogen H2 and the nitrogen in a volume ratio of 3:1. It still contained up to 5% by volume of ammonia.

The burner BR in the heating chamber HK was fed with the biogas BG produced in the biodigester BK, i.e. renewable energy, the inflow of which was regulated by the electronically controlled flow valve V3, air L as oxidant, the inflow of which was regulated by the electronically controlled flow valve V4, and optionally by the gas mixture taken from the line for the hydrogen-nitrogen mixture H2/N2 LH2/N2, the inflow of which was regulated by the electronically controlled flow valve V2. The ignition of the flame was piezoelectric. The air L was passed through the recuperator WT2, wherein it was heated by the hot gas mixture H2/N2. In the process, the temperature of the H2/N2 gas mixture dropped to 100° C.

The gas mixture H2/N2 containing ammonia was cooled down to 55° C. in a cooling device (not shown) after the recuperator WT2. Before the gas mixture H2/N2 entered the hydrogen-nitrogen distributor HV in the biodigester BK, the ammonia was bound by activated carbon impregnated with phosphoric acid. The resulting activated carbon/ammonium phosphate by-product was itself a valuable product and could be used, for example, to produce terra preta.

In another embodiment, the cooled gas mixture H2/N2 was passed through sulfuric acid, wherein the ammonia was bound as ammonium sulfate. The ammonium sulfate solution also represented a valuable product and could be used, for example, as a liquid fertilizer.

In still another embodiment, the hydrogen H2 was separated from the cooled, ammonia-containing gas mixture H2/N2 with the aid of a module (not shown) with hydrogen-selective SEPURAN® Noble membranes from Evonik, fed at a pressure of about 1.5 bar into the hydrogen distributor HV, from where it escaped from the hydrogen nozzles HD into the fermentation liquid GF. Some of the hydrogen H2 could also serve as fuel for the ammonia cracker AC.

The entire BKA biodigester plant was centrally controlled by the electronic data processing system. The control signals were determined by temperature and pressure gauges, gas flow meters, hydrogen sensors HS, ammonia sensors and biogas sensors. The control signals were sent via output lines (not shown for clarity) to the actuators of the valves V1, V2, V3 and V4.

The ammonia NH3 and the hydrogen H2 needed to produce it, as well as the energy for the ammonia cracker AC, were produced using renewable energy from solar energy, such as photovoltaics, solar thermal, solar chemical and updraft power plants, bioenergy from biomass in various forms, such as vegetable oil, wood, biodiesel, bioethanol, cellulose-ethanol, biogas, BtL (biomass-to-liquid) fuels, and biohydrogen; hydropower, such as dams and barrages, run-of-river power plants, watermills, power buoys, ocean wave energy, ocean current energy, and ocean heat; and wind energy, such as wind turbines, airborne wind turbines, and windmills.

1.3 Conclusion

The biodigester plant BKA according to the invention had the essential advantage that hydrogen could be produced in it specifically as required from ammonia, so that all problems of stockpiling hydrogen were avoided from the outset, since the ammonia could be stockpiled in large quantities without any problems at comparatively low pressure. In particular, the hydrogen produced allowed carbon dioxide to be digested to methane and water, resulting in biogas BG of particularly high quality with a methane content of ≥99 vol % measured with the aid of a methane sensor. Since the ammonia cracker AC could furthermore be heated with the generated biogas BG and additionally with the hydrogen-nitrogen mixture H2/N2 and/or hydrogen H2, the biodigester plant BKA according to the invention was particularly energy-efficient.

The essential advantage of the BKA biodigester plant according to the invention, however, was its carbon dioxide-neutrality. It could also be designed in such a way that it even served as a carbon dioxide sink.

FIG. 2

2. Floats SCH with Activated Carbon Masses K

FIG. 2 shows the top view of the longitudinal section through a liquid-permeable float SCH with pellets PK of activated carbon masses K. The floats SCH could be excellently used in the biodigester BK of the biodigester plant BKA according to the invention.

The float SCH had a 12-cornered outline and was advantageously used in the bioreactor BK of FIG. 1. It consisted of a slightly convex shaped lid DE and a slightly convex shaped can DO, both held together by a circumferential spring-groove joint FNV, and was filled with pellets PK of activated charcoal mass K. The charcoal mass K was the beech wood charcoal described in the Manufacturing Example 1. The float SCH had an outer diameter of 10 cm and an inner diameter of 9 cm. Its wall thickness was therefore 0.5 cm. The distance from the central platform of the lid DE to the side edges was at 9 cm. The length of each of the side edges was 8 cm. The corners and the edges were slightly rounded (not shown). The walls of the float SCH had openings O through which the hydrogen H2 or the hydrogen-nitrogen mixture H2/N2 and the fermentation liquid GF flowed in and came into contact with the pellets PK. The formed biogas BG could escape through the openings O in the lid DE into the gas space G of the reactor volume RV.

The SCH floats were manufactured by injection molding from an impact-resistant acrylonitrile-butadiene-styrene copolymer. On the one hand, this embodiment of the floats SCH achieved a comparatively dense covering of the surface OF of the fermentation liquid GF. On the other hand, this covering was not so dense that escape of the biogas BG was impeded.

FIG. 3

3. Carbon Dioxide-Neutral Biodigester Plant BKA for a Multi-Stage Digestion Process.

3.1 Preliminary Remark

The carbon dioxide-neutral biodigester plant BKA for the multistage digestion process according to the invention comprised the biodigesters BK1. BK2 and BK3. These were of common and known design as described in the FIG. 1. The carbon dioxide-neutral biodigester plant BKA was designed for a capacity of 75 kW$_{el}$ and an annual yield of 643,000 kWh of electricity.

For the 4th phase: methanogenesis or methane-forming phase, the microorganisms listed in the description of the FIG. 1 were used.

The biomass BMZ used was a mixture of the farm manures, cattle manure, pig manure, cow manure, poultry manure, and horse manure excluding straw, corn silage, whole-plant grain silage (GPS), green rye silage, cereal grains, grass silage, sugar beets, and fodder beets.

3.2 The BK1 Biodigester

The biodigester BK1 was designed for the 1st phase: hydrolysis, the 2nd phase: acidogenesis or acidifying phase and the 3rd phase: acidogenesis or vinegar forming phase. The fermentation liquid GF in the reactor volume RV had a pH <7.

The liquid-solid biomass BM was introduced via the biomass feed BMZ into the fermentation liquid GF stirred with a paddle stirrer. In the lower part of the reactor volume RV, the gaseous biomass BMG, in the present embodiment landfill gas, was fed through the biomass feed BGZ into the annular distributor BMGV for the landfill gases BMG, from which they exited in the form of gas bubbles that dissolved in the fermentation liquid GF.

Hydrolysis was initially initiated by various types of exoenzymes secreted by microorganisms. The resulting low molecular weight oligo- and monosaccharides, amino acids, fatty acids and glycerol were converted to lower fatty acids, carboxylic acids, especially acetic acid, alcohols, hydrogen sulfide, ammonia, hydrogen and carbon dioxide by acidogenic microorganisms in the acidogenesis. In the acidogenesis, the lower fatty acids and carboxylic acids as well as the lower alcohols were converted to acetic acid by acetogenic microorganisms.

The resulting gaseous fermentation products BG1, which consisted mainly of carbon dioxide and hydrogen, were pumped from the gas space G through the pipeline LBG1 with the help of the injector 7 through the three-way valve 7.1 into the biodigester BK2 and exited from the annular carbon dioxide manifold CO2V as gas bubbles CO2.

In another process, carbon dioxide-containing exhaust gases CO2 from lime kilns were pumped through the pipeline LCO2 by means of the injector 8 to the electronically controlled three-way valve 7.1 for carbon dioxide sequestration and mixed there with the gaseous fermentation products BG1. The resulting gas mixture was also passed through the gas mixture line LGM to the carbon dioxide distributor CO2V. In still another embodiment of the process, a gas mixer not shown was used instead of the three-way valve 7.1. Heat energy was extracted from the hot exhaust gases CO2 of the lime kilns by heat exchangers (not shown) and used to heat the fermentation liquids GF.

The digested liquid-solid fermentation products KBM were pumped into the bottom chamber of the biodigester BK2 at the reactor bottom RB of the biodigester BK1 with the help of the thick matter pump 1 through a connecting pipeline.

3.3 The Biodigester (BK2)

In the biodigester BK), the 4th phase, i.e. methanogenesis, took place. The fermentation liquid GF contained activated carbon microparticles K loaded with hydrogenotrophic and methanogenic archaea. A hydrogen-nitrogen mixture H2/N2 cooled to 50° C., which had been produced and freed from ammonia by the ammonia cracker AC (cf. FIG. 1), was pumped through the hydrogen-nitrogen line LH2/N2 at a pressure of 10 bar into the annular hydrogen-nitrogen distributor HV arranged below the carbon dioxide distributor CO2V with the aid of the injector 6. There, the gas mixture H2/N2 exited as fine gas bubbles into the fermentation liquid GF, which bubbles were mixed with the carbon dioxide bubbles CO2 and the activated carbon microparticles K. The rising gas bubbles dissolved in the fermentation liquid GF, and the biogas BG resulting from methanogenesis accumulated in the gas space G.

The hydrogen probe HS1 located in the gas compartment G was used to measure the hydrogen content of the biogas BG. The measured values were sent via the input signal line SLI1 to the central electronic data processing system ES, which regulated the feed of the hydrogen-nitrogen gas mixture LH2/N2 by the control signals sent via the output signal line SLO.

The biogas BG was fed from the biodigester BK2 into the biogas collection line BGS.

The resulting digested liquid-solid fermentation products KBM, together with part of the activated carbon microparticles K, were conveyed from the bottom space of BK2 to the bottom space of the secondary fermenter BK3 via a connecting pipeline with the aid of the thick matter pump 2.

3.4 The Secondary Digester BK3 and the Solid-Liquid Separator FFS

The secondary digester BK3 served to complete the methanogenesis and thus increase methane yield.

The hydrogen content of the biogas BG was measured with the hydrogen probe HS2 located in the gas compartment G of BK3. The measured values were sent via the input signal line SLI2 to the central electronic data processing system ES, which regulated the feed of the hydrogen-nitrogen gas mixture LH2/N2 into the biodigester BK2 by the control signals sent via the output signal line SLO.

The biogas BG; CH4 that had accumulated in the gas space G was also fed into the biogas collection line BGS and to the biogas discharge line BGA, from where it was sent for further use.

The post-fermented digested liquid-solid fermentation products KBM were pumped into the solid-liquid separator FFS together with part of the activated carbon microparticles K from the bottom space of BK3 with the help of the thick matter pump 3. Therein, the liquid digested fermentation products KBM were separated from the solid digested fermentation products KBM. The latter were discharged via a common and known solid discharger FA for further use as fertilizer or for the production of terra preta.

Figure 4:
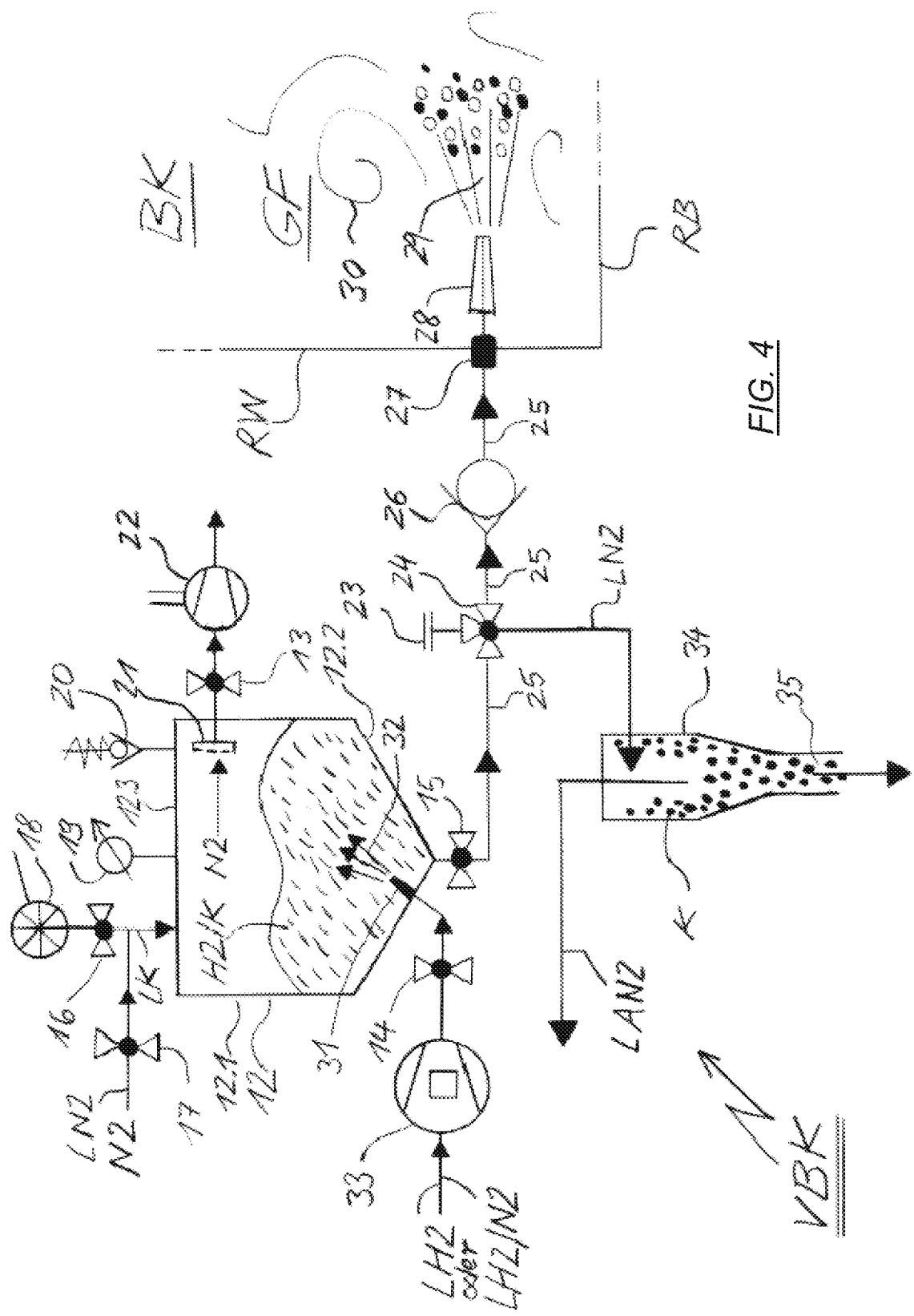
FIG. 4 the top view of a schematic diagram of a device V BKA for treating activated coal masses (K; KM) with hydrogen (H2) at higher pressure and for injecting hydrogen-containing activated coal masses (H2K; H2KM) into the fermentation liquid of biodigesters.

The liquid digested fermentation products KBM could be conveyed to the bottom chambers of the biodigesters BK3; BK2; BK1 through the return lines GFR1; GFR2; GFR with the help of the thick matter pumps 4; 5 at the appropriate position of the three-way valves 9; 10 and the passage valve 11, 3.5 Conclusion The resulting biogas had a methane content of 99% by volume. The low levels of hydrogen H2 further increased the caloric value. A significant advantage of the carbon dioxide-neutral biodigester plant BKA was that it was also excellently suited for the sequestration of carbon dioxide CO2). FIG. 4

4. The Device VBK for the Treatment of Activated Coal Masses K with Hydrogen (H2)

The device VBK for the treatment of activated carbon masses K with hydrogen H2 was constructed of pressure-resistant stainless steel. For the treatment, a powder of carbon microparticles K activated with hydrogenotrophic and methanogenic archaea was first filled into the pressure vessel 12 by means of a rotary valve 18 through the pipeline LK and the opened passage valve 16. During this process, the passage valves 14; 15; 17 in the hydrogen or hydrogen-nitrogen line LH2; LH2/N2 in the pressure line 25 and in the nitrogen purge line LN2 were closed. The pressure vessel 12 had a volume of 100 L and had a tubular upper section 12.1 and a tapered lower section 12.2. It was closed with a convex, removable, pressure- and vacuum-tight lid 12.3. The pipeline LK was routed through the lid 12.3. In addition, a pressure gauge 19 and a safety and pressure retaining valve 20 were arranged on the lid 12.3.

After filling, the passage valve 16 was closed, and the pressure vessel 12 was evacuated through the sieve 21 with the aid of the vacuum pump 22 after opening the shut-off valve 13 for vacuum and overpressure until a vacuum <1.0 mbar was reached. Then the shut-off valve 13 was closed, and the hydrogen-nitrogen mixture (H2/N2) was pumped under pressure by the compressor 33 through the opened passage valve 14 to the spray lance 31 and sprayed therefrom as a spray cone 32 into the powdered bulk of the activated carbon microparticles K. In the process, these were violently swirled. After a pressure of 50 bar was reached, the valve 14 was closed and the hydrogen-nitrogen mixture H2/N2 was allowed to act on the activated carbon microparticles K for 30 minutes. As a result, the pressure in the pressure vessel 12 decreased by 5 bar. After the rest period, the passage valve 15 and the three-way valve 24 were opened to the check valve 26, and the contents of the pressure vessel 12 were blown through the pressure line 25 to the spray lance 28 and sprayed as a spray cone 29 of hydrogen-containing, powdered activated carbon masses H2K and gas bubbles from the hydrogen/nitrogen mixture H2/N2 into the fermentation liquid GF of the biodigester BK. In the process, numerous vortices formed in the fermentation liquid GF, which promoted the mixing of the substances. The feedthrough 27 of the pressure line 25 through the reactor wall RW was sealed fluid-tight with a flexible gasket to cushion the pressure surges during injection. After pressure equalization, the check valve 26 closed. The three-way valve 24 was now opened to the nitrogen purge line LN2 leading to the cyclone 34 and closed in the direction of the check valve 26. The passage valve 17 was opened and nitrogen N2 was blown through the nitrogen purge line LN2, the line LK, the pressure vessel 12, the passage valve 15, the pressure line 25, the three-way valve 24 and through the nitrogen purge line LN2 into the cyclone 34, wherein remnants of the hydrogen-containing powdered activated carbon H2K masses were separated from the gaseous phase and passed via the solids discharge 35 into a collection vessel (not shown). The nitrogen was discharged via the nitrogen outlet line LAN2.

In the injection process according to the invention, significantly more hydrogen H2 was taken up by the powdered activated carbon microparticles K than usual, despite the low affinity between hydrogen H2 and activated carbon K. Moreover, the contact between hydrogen H2 and the hydrogenotrophic and methanogenic archaea was significantly enhanced, which greatly accelerated the fermentation or digestion.

I claim:

1. A carbon dioxide-neutral biodigester plant, comprising:
   a) a biodigester for carbon dioxide-neutral, single-stage or multi-stage production of biogas by fermentation of biomass in a fermentation liquid agitated in presence of
      i) elemental hydrogen,
      ii) hydrogenotrophic and methanogenic archaea, and
      iii) activated carbon masses,
   b) a source of ammonia connected to a first ammonia line,
   c) an ammonia cracker to produce hydrogen or a hydrogen-nitrogen mixture by catalytic cracking of ammonia,
   d) a first hydrogen line for feeding the produced hydrogen or the hydrogen-nitrogen mixture directly into the biodigester, and
   e) a treating device for treating activated coal masses with hydrogen at higher pressure comprising:
      e1) a pressure line and
      e2) a treating spray lance wherein hydrogen-containing activated coal masses configured as spray cones are injected into the fermentation liquid of the biodigester, wherein ammonia from the source of ammonia is produced with power at least in part by renewable energies and the ammonia cracker is powered at least in part by renewable energies, wherein the ammonia cracker is configured as a double-tube reactor, the ammonia cracker comprising:

c1) a central tube with a heat source arranged in the central tube, the heat source comprising a heating chamber with a metallic packed bed, a burner, and a flame, c2) a cracking tube with a cracking catalyst contained in the cracking tube, c3) a pressure reducer with an electronically controlled actuator, c4) a second ammonia line to a first recuperator for heating ammonia with hot exhaust gas supplied from the central tube via an exhaust gas line, c5) a third ammonia line for supplying the heated ammonia from the first recuperator to the cracking tube containing the cracking catalyst c6) a second hydrogen line for discharging the produced hydrogen or the hydrogen-nitrogen mixture from the cracking tube to a second recuperator for heating air fed to the burner and for cooling the produced hydrogen or the hydrogen-nitrogen mixture, c7) a cooling device for further cooling the hydrogen-nitrogen mixture or the hydrogen separated with the aid of a hydrogen-selective membrane to below 70° C., and c8) a separating device for separating ammonia from the produced hydrogen or hydrogen-nitrogen mixture before its introduction into a hydrogen-nitrogen distributor of the biodigester and before its introduction into the treating device for treating activated coal masses with hydrogen at a higher pressure.

2. The carbon dioxide-neutral biodigester plant according to claim 1, wherein the source of ammonia is at least one pressurized gas cylinder.

3. The carbon dioxide-neutral biodigester plant according to claim 1, wherein the burner is operable with hot air as an oxidant and at least one fuel selected from the group consisting of:

(i) biogas, (ii) biogas-natural gas mixtures, (iii) hot hydrogen, and (iv) hot hydrogen-nitrogen gas mixture.

4. The carbon dioxide-neutral biodigester plant according to claim 1, wherein at least one of:

(i) the first ammonia line, (ii) the second ammonia line, (iii) the third ammonia line, (iv) the first hydrogen line, and (v) the second hydrogen line, is spirally shaped.

5. The carbon dioxide-neutral biodigester plant according to claim 1, wherein the biodigester comprises at least one of:

(a1) a liquid-solid biomass inlet for liquid-solid biomass into an upper region of a reactor volume into a gas phase or into moving fermentation liquid, (a2) a gaseous biomass inlet for gaseous biomass into moving fermentation liquid in a lower region of the reactor volume, and (a3) an outlet with one thick matter pump for digested biomasses or fermentation products at a reactor bottom.

6. A process for production of biogas comprising the process steps of:

(a) supplying ammonia, (b) producing hydrogen or a hydrogen-nitrogen mixture by catalytic cracking of ammonia, (c) feeding the produced hydrogen or the hydrogen-nitrogen mixture into a biodigester, (d) treating activated coal masses with hydrogen at higher pressure, and (e) fermenting biomass in a fermentation liquid agitated in the presence of elemental hydrogen, hydrogenotrophic and methanogenic archaea microorganisms and activated carbon masses, wherein steps (a) through (e) are performed with the carbon dioxide-neutral biodigester plant of claim 1.

7. A process for injecting hydrogen-containing powdered activated carbon masses into a fermentation liquid of the biodigester of the carbon dioxide-neutral biodigester plant according to claim 1 under pressure, comprising the steps of:

(a) providing a treatment device for the treatment of activated coal or carbon masses with hydrogen at high pressure, the treatment device comprising a pressure vessel with a tubular upper region, a conically tapering lower region, a horizontally extending cover, a passage valve for hydrogen-containing activated carbon masses, a pressure gauge, a safety valve or pressure holding valve, a nitrogen purge line with nitrogen passage valve for nitrogen to the pressure vessel, and a metering device for powdered activated carbon masses with a powdered activated carbon masses line for the powdered, activated coal masses to the pressure vessel, (b) filling of powdery, activated carbon masses with the aid of the metering device via the powdered activated carbon masses line into the one pressure vessel with the passage valve closed, (c) evacuating the pressure vessel with the passage valve closed using a vacuum pump with an upstream shut-off valve for vacuum and overpressure and an upstream strainer within the pressure vessel until a vacuum ≤1.0 mbar is reached, (d) closing the upstream shut-off valve and spraying hydrogen or hydrogen/nitrogen mixture under higher pressure into the lower region of the pressure vessel with the treating spray lance in the form of a spray cone until a pressure ≥10 bar is reached, conducting either (i) hydrogen through a first hydrogen line or (ii) hydrogen/nitrogen mixture through a second hydrogen line to a one compressor, (e) compressing the hydrogen or hydrogen/nitrogen mixture and conveying the compressed hydrogen or hydrogen/nitrogen mixture through an upstream passage valve to the treating spray lance, and (f) closing the upstream passage valve and opening the passage valve to a pressure line with a check valve and the sealed feedthrough for the pressure line through the reactor wall and passing the hydrogen-containing powdery activated carbon mass to a second spray lance and injecting the hydrogen-containing powdered activated carbon mass in the form of a spray cone of hydrogen and hydrogen-containing powdered activated carbon mass.

8. The process according to claim 7, further comprising the steps of:

(g) turning a three-way valve in the discharge line after pressure equalization so that the discharge line is closed in the direction of the check valve and open in the direction of the nitrogen purge line and a centrifugal separator, and (h) opening the nitrogen passage valve for nitrogen in the nitrogen purge line and purging the pressure vessel, the pressure line, the three-way valve, and the downstream nitrogen purge line, separating any powdery carbon masses in the centrifugal separator and discharging them from a solids discharge, and discharging the nitrogen from the centrifugal separator through a nitrogen discharge line.

9. The carbon dioxide-neutral biodigester plant according to claim 1, wherein an output of the biodigester plant is an ammonium sulfate solution usable as liquid fertilizer.

10. The carbon dioxide-neutral biodigester plant according to claim 1, wherein an output of the biodigester plant is an activated carbon/ammonium phosphate byproduct usable to produce terra preta.

11. A carbon dioxide-neutral biodigester plant, comprising:

a) a biodigester for carbon dioxide-neutral, single-stage or multi-stage production of biogas by fermentation of biomass in a fermentation liquid agitated in presence of
   i) elemental hydrogen,
   ii) hydrogenotrophic and methanogenic archaea, and
   iii) activated carbon masses,
b) a source of ammonia connected to a first ammonia line,
c) an ammonia cracker to produce hydrogen or a hydrogen-nitrogen mixture by catalytic cracking of ammonia,
d) a first hydrogen line for feeding the produced hydrogen or the hydrogen-nitrogen mixture directly into the biodigester, and
e) a treating device for treating activated coal masses with hydrogen at higher pressure comprising:
   e1) a pressure line and
   e2) a treating spray lance
   e3) a pressure vessel with a tubular upper section, a tapered lower section, a horizontally extending ceiling, and a passage valve for hydrogen-containing activated carbon masses,
   e4) a vacuum pump with an upstream shut-off valve for vacuum and overpressure and an upstream strainer inside the pressure vessel,
   e5) a pressure gauge and a safety valve or pressure retaining valve,
   e6) a nitrogen purge line with a passage valve for nitrogen to the pressure vessel,
   e7) a metering device for powdered, activated carbon masses with a powered, activated carbon masses line for the powdered, activated carbon masses to the pressure vessel, and e8) a lower section spray lance for hydrogen or hydrogen-nitrogen mixture in the tapered lower section, a third hydrogen line for hydrogen or hydrogen-nitrogen mixture, a compressor and an upstream passage valve, wherein hydrogen-containing activated coal masses configured as spray cones are injected into the fermentation liquid of the biodigester, and wherein ammonia from the source of ammonia is produced with power at least in part by renewable energies and the ammonia cracker is powered at least in part by renewable energies.

12. A carbon dioxide-neutral biodigester plant, comprising:

a) a biodigester for carbon dioxide-neutral, single-stage or multi-stage production of biogas by fermentation of biomass in a fermentation liquid agitated in presence of
   i) elemental hydrogen,
   ii) hydrogenotrophic and methanogenic archaea, and
   iii) activated carbon masses,
b) a source of ammonia connected to a first ammonia line,
c) an ammonia cracker to produce hydrogen or a hydrogen-nitrogen mixture by catalytic cracking of ammonia,
d) a first hydrogen line for feeding the produced hydrogen or the hydrogen-nitrogen mixture directly into the biodigester, and
e) a treating device for treating activated coal masses with hydrogen at higher pressure comprising:
   e1) a pressure line and
   e2) a treating spray lance
wherein hydrogen-containing activated coal masses configured as spray cones are injected into the fermentation liquid of the biodigester, wherein ammonia from the source of ammonia is produced with power at least in part by renewable energies and the ammonia cracker is powered at least in part by renewable energies, wherein the activated carbon masses in the fermentation liquid of the biodigester are present in at least one of:

f1) suspended bodies freely movable or fixed by anchors to a reactor bottom, the suspended bodies comprising:
   (i) at least one float,
   (ii) at least one fixed, activated carbon mass and
   (iii) at least one weight,
f2) floating bodies,
f3) a layer fixed with the help of an adhesive,
f4) fluidizable bodies of a fluidized bed of a three-phase fluidized bed biodigester,
f5) an enclosed immobile, fluid-permeable container,
f6) a fixed bed in a fixed bed reactor located in an upstream side circuit of a two-stage converter, and
f7) the form of magnetizable activated carbon particles.

* * * * *